United States Patent [19]
Simmons et al.

[11] Patent Number: 5,677,136
[45] Date of Patent: Oct. 14, 1997

[54] METHODS OF OBTAINING COMPOSITIONS ENRICHED FOR HEMATOPOIETIC STEM CELLS, COMPOSITIONS DERIVED THEREFROM AND METHODS OF USE THEREOF

[75] Inventors: Paul J. Simmons, Adelaide, Australia; Beth L. Hill, Mountain View; Benjamin P. Chen, Fremont, both of Calif.

[73] Assignee: Systemix, Inc., Palo Alto, Calif.

[21] Appl. No.: 340,047

[22] Filed: Nov. 14, 1994

[51] Int. Cl.$^6$ .............................. C07K 16/28; C12N 5/08; C12Q 1/24
[52] U.S. Cl. ..................... 435/7.24; 435/2; 435/30; 435/240.2; 435/240.27; 530/388.7
[58] Field of Search ..................... 435/2, 7.24, 30, 435/240.2, 240.27; 530/388.7

[56] References Cited

U.S. PATENT DOCUMENTS

| | | | |
|---|---|---|---|
| 4,714,680 | 12/1987 | Civin | 435/240.25 |
| 5,061,620 | 10/1991 | Tsukamoto et al. | 435/7.21 |
| 5,147,784 | 9/1992 | Peault | 435/7.24 |
| 5,468,612 | 11/1995 | Cohen et al. | 435/6 |

FOREIGN PATENT DOCUMENTS 0341966  11/1989  European Pat. Off. .

OTHER PUBLICATIONS

Baum et al., "Isolation of a candidate human hematopoietic stem-cell population" *Proc. Natl. Acad. Sci. USA* (1992) 89:2804–2808.

Chaudhary et al., "Expression and activity of P-glycoprotein, a multidrug efflux pump, in human hematopoietic stem cells" *Cell* (1991) 66:85–94.

Spangrude et al.,"Purification and characterization of mouse hematopoietic stem cells" *Science* (1988) 241:58–62.

Smith et al., "Clonal analysis of hematopoietic stem-cell differentiation in vivo" *Proc. Natl. Acad. Sci. USA* (1991) 88:2788–2792.

Uchida, "Characterization of mouse hematopoietic stem cells (bone marrow cells)" *Dialog™ Dissertation Abstact* (1992) Ph.D. Thesis, Stanford University, 2 pages total.

Whitlock et al., "Long-term culture of B lymphocytes and their precursors from murine bone marrow" *Proc. Natl. Acad. Sci. USA* (1982) 79:3608–3612.

Whitlock et al., "Bone marrow stromal cell lines with lymphopoietic activity express high levels of a pre-B neoplasia–associated molecule" *Cell* (1987) 48:1009–1021.

Štefanová et al., "Association of the CD59 and CD55 cell surface glycoproteins with other membrane molecules" *J.Immunol.* (1991) 147:1587–1592.

Spangrude,"Enrichment of murine haemopoietic stem cells: diverging roads" *Immunol. Today* (1989) 10:344–350.

Sawada et al., "Complementary DNA sequence and deduced peptide sequence for CD59/MEM–43 antigen, the human homologue of murine lymphocyte antigen Ly–6C" *Nucl. Acids Res.* (1989) 17:6728.

Philbrick et al., "The CD59 antigen is a structural homologue of murine Ly–6 antigens but lacks interferon inducibility" *Eur. J. Immunol.* (1990) 20:87–92.

Davies et al., "CD59, an Ly–6–like protein expressed in human lymphoid cells, regulates the action of the complement membrane attack complex on homologous cells" *J. Exp. Med.* (1989) 170:637–654.

Okada et al., "20 KDa homologous restriction factor of complement resembles T cell activating protein" *Biochem. Biophys. Res. Commun.* (1989) 162:1553–1559.

Haugland, *Handbook of Fluorescent Probes and Research Chemicals* Molecular Probes, Inc., 5th ed., (1992–1994). The title page and table of contents are included herewith.

Kyoizumi et al., "Implantation and maintenance of functional human bone marrow in SCID–hu mice" *Blood* (1992) 79:1704–1711.

Chen et al., "Engraftment of human hematopoietic precursor cells with secondary transfer potential in SCID–hu mice" *Blood* (1994) 84:2497–2505.

Köhler et al., "Continuous cultures of fused cells secreting antibody of predefined specificity" *Nature* (1975) 256:495–497.

Simmons et al., "Mechanisms of cytomegalovirus–mediated myelosuppression: Perturbation of stromal cell function versus direct infection of myeloid cells" *Proc. Natl. Acad. Sci. USA* (1990) 87:1386–1390.

Simmons et al.,"Identification of stromal cell precursors in human bone marrow by a novel monoclonal antibody, STRO–1" *Blood* (1991) 78:55–62.

Simmons et al., "Host origin of marrow stromal cells following allogeneic bone marrow transplantation" *Nature* (1987) 328:429–432.

Iscove et al., "Net increase of pluripotential hemapoietic precursors in suspension culture in response to IL–1 and IL–3" *J. Immunol.* (1989) 142:2332–2337.

Haylock et al., "Ex vivo expansion and maturation of peripheral blood CD34$^+$ cells into the myeloid lineage" *Blood* (1992) 80:1405–1412.

To et al., "The optimization of collection of peripheral blood stem cells for autotransplantation in acute myeloid leukaemia" *Bone Marrow Transplant.* (1989) 4:41–47.

Sutherland et al., "Characterization and partial purification of human marrow cells capable of initiating long–term hematopoiesis in vitro" *Blood* (1989) 74:1563–1570.

(List continued on next page.)

*Primary Examiner*—David Saunders
*Attorney, Agent, or Firm*—Morrison & Foerster LLP

[57] ABSTRACT

A method for obtaining human hematopoietic stem cells is provided by enrichment for stem cells using a novel stem cell marker. Compositions enriched for stem cells are obtained using novel antibody HCC-1 which is specific for a CD59 epitope highly accessible on stem cells, and less accessible or absent on mature cells. The enriched population of cells derived from these methods are also provided.

26 Claims, 18 Drawing Sheets

OTHER PUBLICATIONS

Smith et al., "Purification and partial characterization of a human hematopoietic precursor population" *Blood* (1991) 77:2122–2128.

Brandt et al., "Cytokine–dependent long–term culture of highly enriched precursors of hematopoietic progenitor cells from human bone marrow" *J. Clin. Invest.* (1990) 86:932–941.

Andrews et al., "Precursors of colony–forming cells in humans can be distinguished from colony–forming cells by expression of the CD33 and CD34 antigens and light scatter properties" *J. Exp. Med.* (1989) 169:1721–1731.

Terstappen et al., "Sequential generations of hematopoietic colonies derived from single nonlineage–committed $CD34^+$ $CD38^-$ progenitor cells" *Blood* (1991) 77:1218–1227.

Udomsakdi et al., "Separation of functionally distinct subpopulations of primitive human hematopoietic cells using rhodamine–123" *Exp. Hematol.* (1991) 19:338–342.

Rayner et al., "A simple and efficient procedure for generating stable expression libraries by cDNA cloning in a retroviral vector" *Mol. Cell. Biol.* (1994) 14:880–887.

Galy et al.,"Generation of T cells from cytokine–mobilized peripheral blood and adult bone marrow $CD34^+$ cells" *Blood* (1994) 84:104–110.

Galy et al., "Precursors of $CD^+CD4^+CD8^+$ cells in the human thymus are defined by expression of CD34. Delineation of early events in human thymic development" *J. Exp. Med.* (1993) 178:391–401.

L.W.M.M. Terstappen et al, Journal of Leukocyte Biology, 52, 652–660,1992.

PATIENT 1013

PATIENT 487

PATIENT 1507

METHODS OF OBTAINING COMPOSITIONS ENRICHED FOR HEMATOPOIETIC STEM CELLS, COMPOSITIONS DERIVED THEREFROM AND METHODS OF USE THEREOF

TECHNICAL FIELD

The field of this invention is the isolation of a population of cells enriched for human hematopoietic stem cells.

BACKGROUND

Mammalian hematopoietic cells provide a diverse range of physiological activities. These cells are divided into lymphoid, myeloid and erythroid lineages. The lymphoid lineages, comprising B cells and T cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies, provides protection against neoplastic cells, scavenges foreign materials, produces platelets, and the like. The erythroid lineage provides the red blood cells, which act as oxygen carriers.

All publications cited herein are hereby incorporated herein by reference in their entirety.

Despite the diversity of the nature, morphology, characteristics and function of hematopoietic cells, it is presently believed that these cells are derived from a single precursor cell population, termed "stem cells." Stem cells are capable of self-regeneration and may become lineage committed progenitors which are dedicated to differentiation and expansion into a specific lineage. As used herein, "stem cells" refers to hematopoietic cells and not stem cells of other cell types.

A pluripotent stem cell may be defined as follows: (1) gives rise to progeny in all defined hematolymphoid lineages; and (2) limiting numbers of cells are capable of fully reconstituting a seriously immunocompromised host in all blood cell types and their progenitors, including the pluripotent hematopoietic stem cell, by self-renewal.

A highly purified population of stem cells is necessary for a variety of in vitro experiments and in vivo indications. For instance, a purified population of stem cells will allow for identification of growth factors associated with their self-regeneration. In addition, there may be as yet undiscovered growth factors associated with: (1) the early steps of dedication of the stem cell to a particular lineage; (2) the prevention of such dedication; and (3) the negative control of stem cell proliferation.

Stem cells find use in: (1) regenerating the hematopoietic system of a host deficient in any class of hematopoietic cells; (2) a host that is diseased and can be treated by removal of bone marrow, isolation of stem cells and treatment with drugs or irradiation prior to re-engraftment of stem cells; (3) producing various hematopoietic cells; (4) detecting and evaluating growth factors relevant to stem cell self-regeneration; and (5) the development of hematopoietic cell lineages and assaying for factors associated with hematopoietic development.

Stem cells are important targets for gene therapy, where the inserted genes promote the health of the individual into whom the stem cells are transplanted. In addition, the ability to isolate stem cells may serve in the treatment of lymphomas and leukemias, as well as other neoplastic conditions where the stem cells are purified from tumor cells in the bone marrow or peripheral blood, and reinfused into a patient after myelosuppressive or myeloablative chemotherapy. Thus, there have been world-wide efforts toward isolating stem cells in.substantially pure of pure form.

Stem cells constitute only a small percentage of the total number of hematopoietic cells Hematopoietic cells are identifiable by the presence of a variety of cell surface "markers." Such markers may be either specific to a particular lineage or progenitor cell or be present on more than one cell type. Currently, it is not known how many of the markers associated with differentiated cells are also present on stem cells. One marker, which was previously indicated as present solely on stem cells, CD34, is also found on a significant number of lineage committed progenitors. U.S. Pat. No. 4,714,680 describes a population of cells expressing the CD34 marker.

The CD34 marker is found on numerous lineage committed hematopoietic cells. In particular, 80–90% of the $CD34^+$ population is marked by other lineage specific and non-specific markers. In view of the small proportion of the total number of cells in the bone marrow or peripheral blood which are stem cells, the uncertainty of the markers associated with the stem cell as distinct from more differentiated cells, and the general difficulty in assaying for stem cells biologically, the identification and purification of stem cells has been elusive. Characterizations and isolation of stem cells are reported in: Baum et al. (1992) *Proc. Natl. Acad. Sci. USA* 89:2804–2808; and Tsukamoto et al. U.S. Pat. No. 5,061,620.

Decreased rhodamine 123 (rho123) staining of hematopoietic cells appears to correlate to stem cell potential. This so-called "$rho^{lo}$" marker is determined not by the initial dye accumulation but by an efflux process sensitive to P-glycoprotein (P-gp) inhibitors. Retention of several P-gp-transported fluorescent dyes, including rho123, in human bone marrow cells was inversely correlated with the expression of P-gp. Bone marrow cells expressing physical and antigenic characteristics of pluripotent stem cells show high levels of P-BP expression and fluorescent dye efflux. Fractions of human bone marrow cells isolated on the basis of either increased rho123 efflux or P-gp expression contained practically all the primitive progenitor cells of human bone marrow, including long-term culture-initiating cells (LTC-IC). Chaudhary and Roninson (1991) *Cell* 66:85–94.

Recently, the mouse stem cell has been obtained in at least highly concentrated, if not a purified form, where fewer than about 30 cells obtained from bone marrow were able to reconstitute all of the lineages of the hematopoietic system of a lethally irradiated mouse. Each assayed cell is multipotent for all hematopoietic lineages, while self-renewal is variable amongst these cells. Spangrude et al. (1988) *Science* 241:58–62; Smith et al. (1991) *Proc. Natl. Acad. Sci. USA* 88:2788–2792; Uchida (1992) Ph.D. Thesis Stanford U.; and see also, EPA 89 304651.6 and the references cited therein which describe the isolation of mouse stem cells.

SUMMARY OF THE INVENTION

Methods resulting in the isolation from populations of hematopoietic cells of compositions enriched for stem cells are provided. The methods employ a separation regimen utilizing an antibody specific for a unique epitope on the CD59 cell surface protein that is accessible to a high degree on stem cells ($CD34^+HCC-1^+$), while being less accessible or absent on more mature cells ($CD34^+HCC-1^{lo/-}$).

Positive selection of stem cells with antibodies which recognize this epitope is used in combination with selection for cells expressing the CD34 marker to obtain a cell population enriched for stem cells. Negative selection is used independently, or in conjunction with one or both of the above methods, in a stem cell enrichment scheme. The enriched population of cells derived from these methods are also provided and are designated CD34$^+$HCC-1$^+$.

Figure 1A:
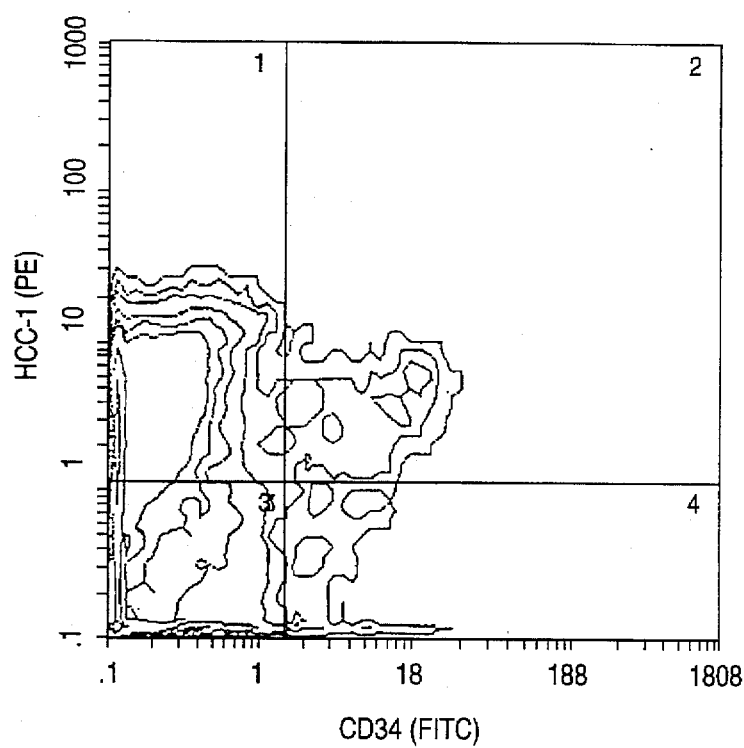
FIG. 1 depicts fluorescence plots showing coexpression of CD34 and HCC-1 on bone marrow mononuclear cells (BMMNC). (A) is a two-color fluorescence plot of CD34 and HCC-1 expression on BMMNC. (B) shows contour plots of the light scatter properties of CD34$^+$, CD34$^+$HCC-1$^+$, and CD34$^+$HCC-1$^-$ cell populations.

Panel A is normal BM. Panel B is patient 3. Panel C is patient 13. Panel D is patient 19. Panel E is patient 31. Panel F is patient 32. Panel G is patient 33.

FIG. 8 depicts the results of FACS analyses of the phenotypes of CD34$^+$HCC-1$^+$ cells from cadaveric bone marrow. (A) depicts the separation of CD34$^+$ cells into HCC-1$^{lo/-}$ and HCC-1$^{hi}$ populations. (B) depicts cells sorted on the lymphoblastoid gate into HCC-1$^{lo/-}$ and HCC-1$^{hi}$. (C) depicts forward and side scatter profile of cells separated on the HCC-1$^{lo/-}$ gate. (D) depicts HCC-1$^{lo/-}$ cells separated by Thy-1 expression. (E) depicts forward and side scatter profile of cells sorted on the HCC-1$^{hi}$ gate. (F) depicts cells HCC-1$^{hi}$ cells sorted by Thy-1 expression.

FIG. 9 depicts the results of AC6.21 coculture using CD34$^+$ bone marrow cells sorted into CD34$^{+HCC-1hi}$ and CD34$^{+HCC-1lo/-}$ populations. The frequency of cobblestone area forming cells (CAFC) for each population is compared. The results show that HCC-1 splits CD34$^+$ cells into equal sized subsets and enriches the CAFC activity 2–3 fold. Panel A shows CAFC activity of HCC-1$^{hi}$/CD34$^+$, HCC-1$^{lo}$/CD34$^+$ and CD34$^+$ cells. Panel B shows activity of HCc-1$^{hi}$/CD34$^+$ and CD34$^+$ cells.

Figure 10:
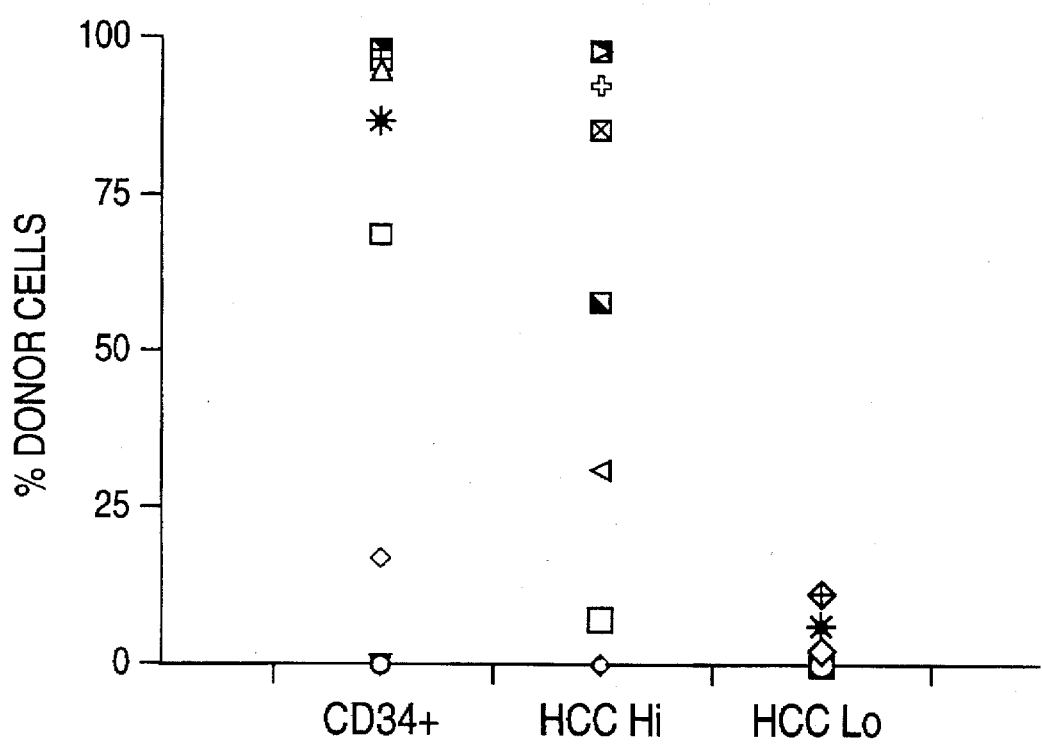
Figure 11A:
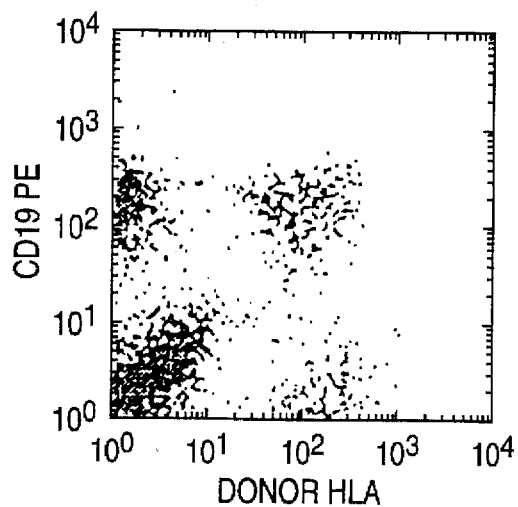
Figure 11B:
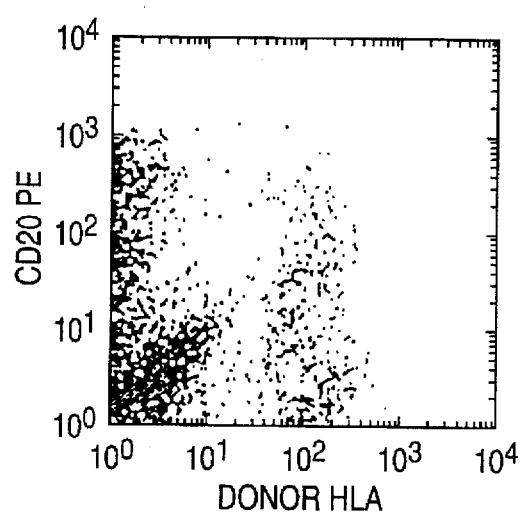
Figure 11C:
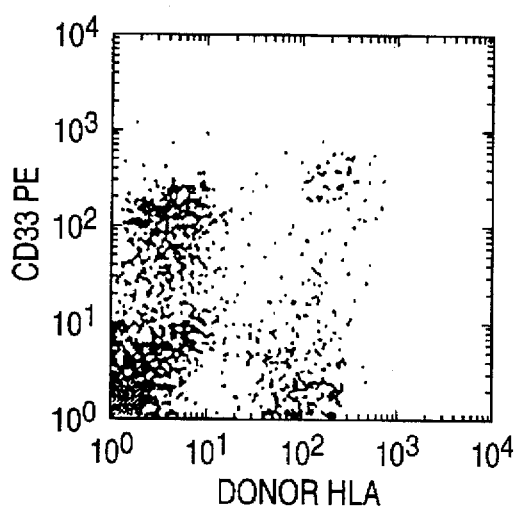
Figure 11D:
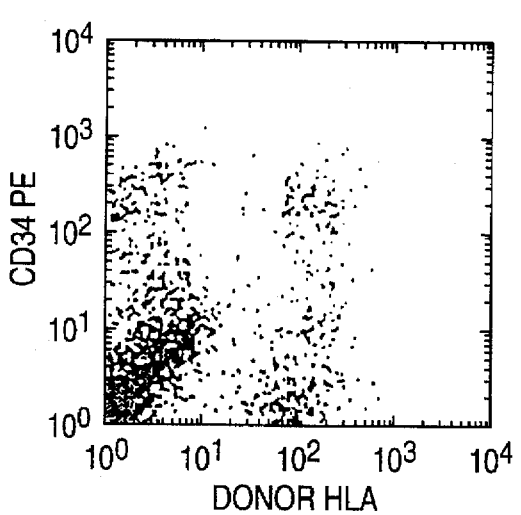
Figure 11E:
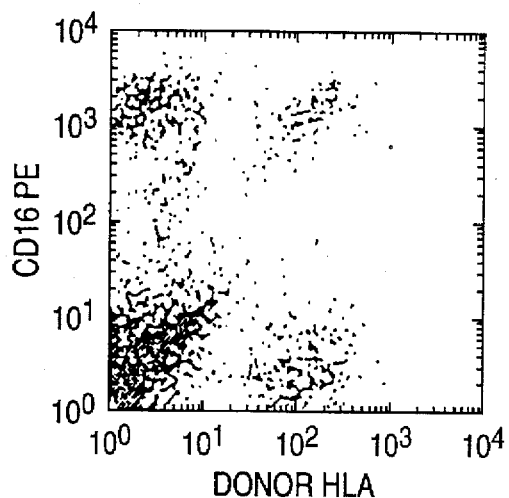
Figure 11F:
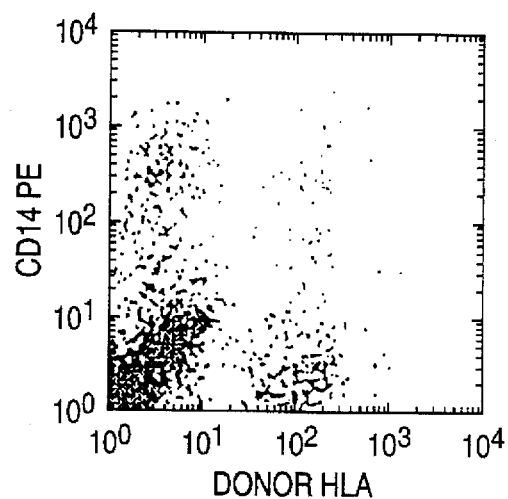
Figure 11G:
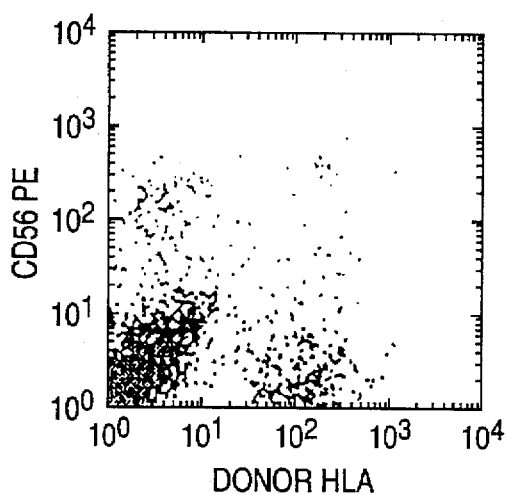
Figure 11H:
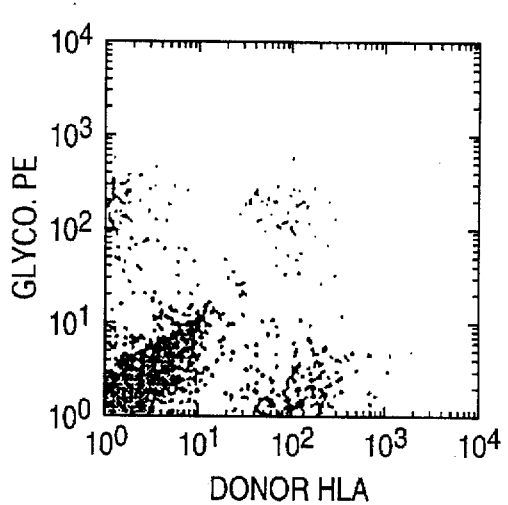
Figure 12A:
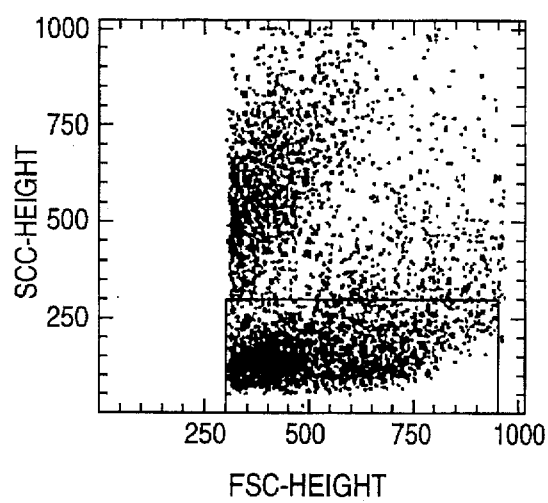
Figure 12B:
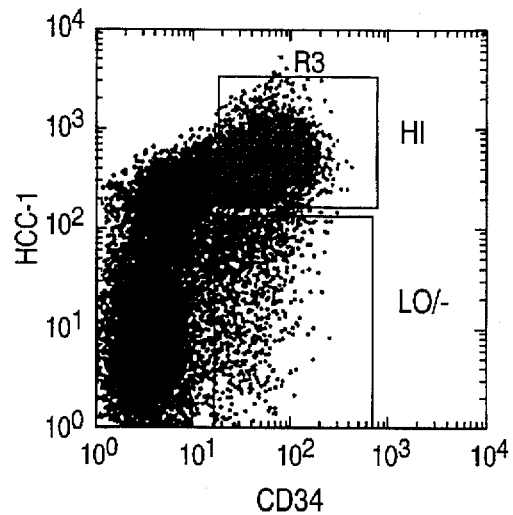
Figure 12C:
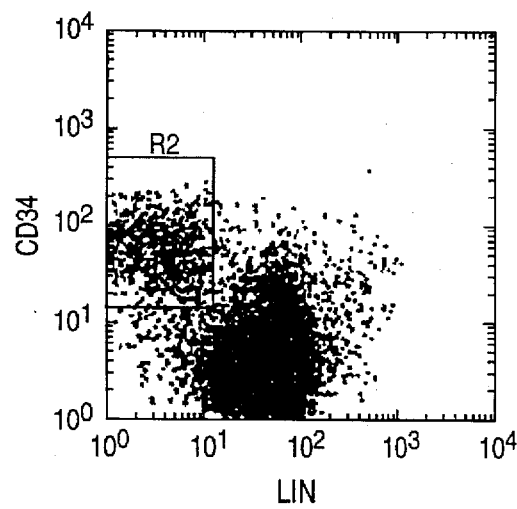
Figure 12D:
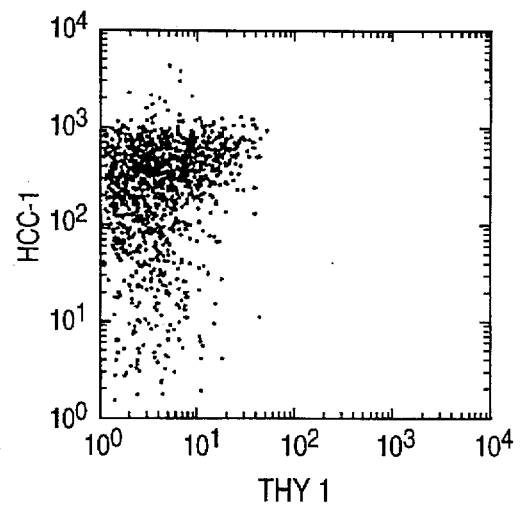
Figure 13A:
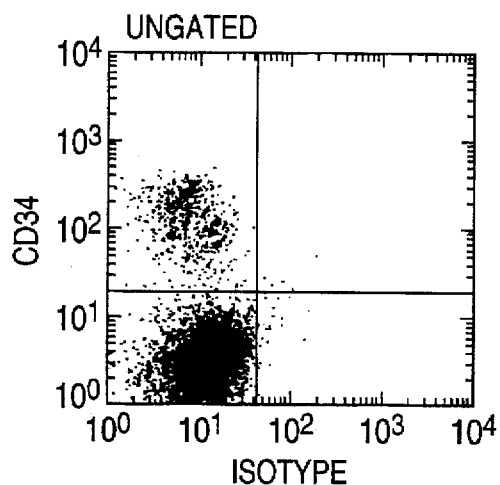
Figure 13B:
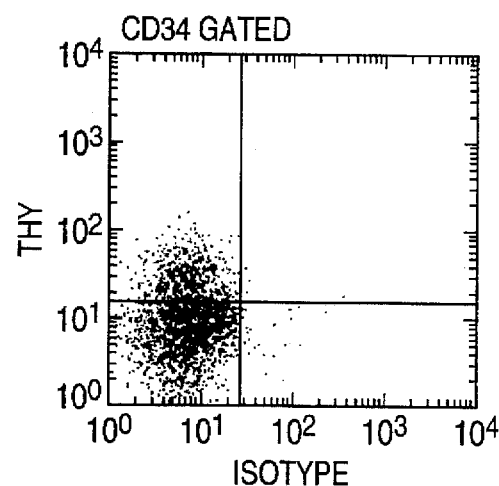
Figure 13C:
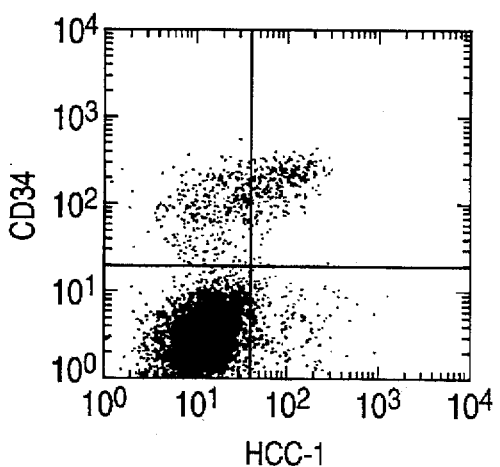
Figure 13D:
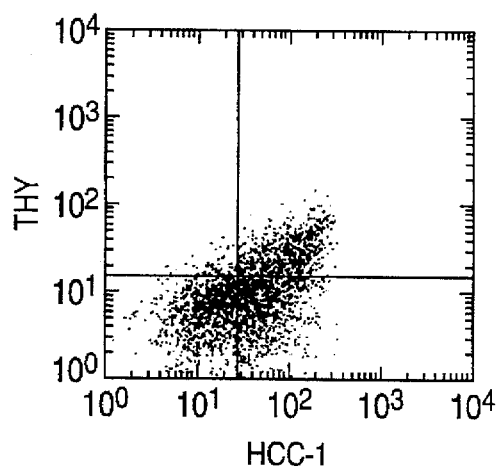

FIG. 10 depicts the results of SCID-hu thymus assays with CD34$^+$ cell populations sorted into CD34$^{+HCC-1hi}$ and CD34$^{+HCC-1lo/-}$. Each point represents the percent of donor cells found six weeks after individual grafts were injected with the indicated cell population.

FIG. 11 depicts the results of a SCID-hu bone assay engrafted with CD34$^{+HCC-1hi}$ cell population. Each panel shows donor HLA on the x-axis and the indicated cell surface marker on the y-axis. Panel A is CD19. Panel B is CD20. Panel C is CD33. Panel D is CD34. Panel E is CD16. Panel F is CD14. Panel G is CD56. Panel H is glycophorin A. The two-color immunofluorescent analysis demonstrates that CD34$^{+HCC-1hi}$ cells are pluripotent, giving rise to lymphoid, myeloid, erythroid and CD34$^+$ progeny.

FIG. 12 depicts co-expression of HCC-1 and Thy1 on CD34$^{+Lin-}$ cadaveric bone marrow cells. (LIN$^-$ is CD2$^-$, CD14$^-$, CD15$^-$, CD19$^-$ and glycophorin A$^-$.) Panel A shows forward scatter (FSC) on the x-axis and side scatter (SSC) on the y-axis; the boxed region represents the cells shown in Panel B. The upper boxed region in Panel B depicts cells which are HCC-1$^{hi}$/CD34$^+$, the lower panel shows HCC-1$^{lo}$/CD34$^+$ cells. Panel C shows cells gated by CD34$^+$ and Lin expression. Panel D shows analysis of CD34$^+$Lin-gated cells stained for HCC-1 and Thy-1 expression.

FIG. 13 depicts the results obtained from peripheral blood apheresis samples from patients treated with Chemotherapy and cytokines to mobilize primitive hematopoietic cells into the periphery and analyzed using immunofluorescence techniques for the coexpression of HCC-1, CD34 and Thy-1 markers. Panel A depicts analysis of cells for CD34 expression. Panel C shows analysis of cells for CD34 and HCC-1 expression. Panel B shows CD34+ gated cells stained for Thy-1, and Panel D shows CD34+ gated cells stained for Thy-1 and HCC-1.

DEPOSIT INFORMATION

The hybridoma producing antibody HCC-1 was deposited with the american Type Culture Collection (ATCC) 12301 Parklawn Drive, Rockville, Md., 20852, U.S.A. on Oct. 18, 1994 under the provisions of the Budapest Treaty on the International Recognition of the Deposit of Microorganisms for the Purposes of Patent Procedure under Accession No. HB 11729.

DESCRIPTION OF THE SPECIFIC EMBODIMENTS

The present invention provides a method for isolating a population of hematopoietic cells highly enriched for stem cells.

Antibodies to cell surface molecules expressed on CD34$^+$ hematopoietic progenitor cell subsets enable the subfractionation of hematopoietic progenitors according to functional capaciLies. CD34$^+$ adult bone marrow cells were sorted according to their reactivity of an epitope of CD59 identified by the monoclonal antibody HCC-1. This subtraction of CD34$^+$ cells is more highly enriched for stem cells compared to. selection with CD34 alone. It has now been found that the CD59 epitope recognized by HCC-1 is expressed at high density on stem cells.

HCC-1 subdivides the CD34$^+$ cell population into approximately equal subpopulations, with the stem cell. activity found entirely in the HCC-1$^+$ subpopulation.. Stem cell activity is further enriched in the CD34$^+$ cells expressing high levels of HCC-1 (HCC-1$^{hi}$). Analyses for hematopoietic progenitors have been reported by Whitlock and Witte (1982) *Proc. Natl. Acad. Sci. USA* 79:3608–3612; and Whitlock et. al. (1987) *Cell* 48:1009–1021. Although the antigen recognized by HCC-1 is CD59, the staining pattern of HCC-1 is distinct from that reported for CD59. CD59 is expressed on most bone marrow cells.

Without being bound by any one theory, the results presented herein indicate that CD59 association with. a cell surface protein of molecular weight=80 KD, gp80, may determine the accessibility of the HCC-1 epitope. In support of this hypothesis, immunoprecipitation of CD59 from cell types which bind. HCC-1 (i.e., fibroblasts) and those which do not (HL60 cells), demonstrates that gp80 co-immunoprecipitates with CD59 only from cells which do not bind HCC-1. Nonetheless, several alternative hypotheses explain the results but are likewise not binding or limiting to the claimed invention. For instance, HCC-1 may bind to a carbohydrate epitope on CD59 such as that predicted at asparagine 18. As the primitive cells differentiate, the glycosylation pattern may change resulting in loss of binding by HCC-1. Alternatively, HCC-1 specific epitopes may be masked or exposed during differentiation by the changing interactions of CD59 with other GPI-linked proteins such as CD55. Stefanova and Horejsi (1991) *J. Immunol.* 147:1587. There are also a large number of GPI-linked proteins which have been described (e.g., CD14, CD15, CD16, CDW17, CD48, CD52, CD55, CD58, CD66, CD67, CD73 and Thy-1) many of which are expressed in a lineage or maturation stage specific manner. Changes of association of CD59 with any other such protein may result in differences of HCC-1 binding.

Simultaneous 5 color flow cytometric analysis shows that the HCC-1$^{hi}$ population includes virtually all CD34$^{+Thy-}$1$^+$ LIN$^-$ cells which have previously been characterized to be primitive pluripotential hematopoietic progenitors. (FIG. 12, FIG. 13) Thus, the HCC-1 epitope is expressed at high levels on a subset of CD34$^+$ cells which contains virtually all primitive hematopoietic stem cells and the HCC-1 monoclonal antibody (and other antibodies recognizing the same epitope) enables the purification of this subset of hematopoietic stem cells.

In addition to being recognized by HCC-1 antibodies, the stem cells described herein may be characterized by the following phenotypes: in the case of fetal cells including, but not limited to, CD34$^+$, CD3$^-$ CD7$^-$, CD8$^-$, CD10$^-$, CD14$^-$, CD15$^-$, CD19$^-$, CD20$^-$, and Thy-1$^+$; and in the case of adult cells including, but limited to: CD34$^+$, CD3$^-$, CD7$^-$, CD8$^-$, CD10$^-$, CD14$^-$, CD15$^-$, CD19$^-$, CD20$^-$, and Thy-1$^+$ or as represented in Table 1. Also, for the human CD34$^+$ cell population, rho123 can divide the cells into high and low subsets ("rho$^{lo}$" and "rho$^{hi}$"). See Spangrude (1989) *Immunology Today* 10:344–350, for a description of the use of rho123 with mouse stem cellS. Preferably the cells are rho$^{1^o}$. Preferably the CD34$^{+HCC-}$1$^+$ cells are human but may derive from any suitable animal.

Preferably, the cells are LIN$^-$. LIN$^-$ cells generally refer to cells which lack markers associated with T cells (such as CD2, 3, 4 and 8), B cells (such as CD10, 19 and 20), myeloid cells (such as CD14, 15, 16 and 33), natural killer ("NK") cells (such as CD2, 16 and 56), RBC (such as glycophorin A), megakaryocytes, mast cells, eosinophils or basophils. The absence or low expression of such lineage specific markers is identified by the lack of binding of antibodies specific to the cell specific markers, useful in so-called "negative selection".

Table 1 summarizes probable phenotypes of stem. cells in fetal, adult, and mobilized peripheral blood. In Table 1, myelomonocytic stands for myelomonocytic associated markers, NK Stands for natural killer cells and AMPB stands for adult mobilized peripheral blood. As used herein, b6th infra, supra and in Table 1, the negative sign or superscript negative sign ($^-$) means that the level of the specified marker is undetectable above Ig isotype controls by FACS analysis, and includes cells with very low expression of the specified marker.

TABLE 1

Probable Stem Cell Phenotypes

| | NK and T cell markers | | | B cell markers | | | Myelomonocytic | | | Other | | | | | | P-gp |
|---|---|---|---|---|---|---|---|---|---|---|---|---|---|---|---|---|
| | CD2 | CD3 | CD8 | CD10 | CD19 | CD20 | CD14 | CD15 | CD16 | CD33 | CD34 | CD38 | HLA-DR | C-Kit | Thy | Rho | Activity |
| FBM | — | — | — | — | — | — | — | — | — | ? | + | — | + | + | + | lo | + |
| ABM | — | — | — | — | — | — | — | — | — | — | + | — | lo/— | + | + | lo | + |
| AMPB | — | — | — | — | — | — | — | — | — | lo/—? | + | ? | lo/— | ? | + | lo | + |

In another embodiment of the invention, a composition highly enriched in stem cells is provided. The results presented herein indicate that HCC-1 antibodies recognize and bind with high specificity to an epitope of the CD59 cell surface antigen found on human hematopoietic cells, and exposed to a high degree on stem cells. This specificity can be used to isolate and purify stem cells. Such a composition has utility in reconstituting human hematopoietic systems and in studying various parameters of hematopoietic cells.

The compositions may be further enriched for stem cells by positive selection for other stem cell specific markers and/or negative selection for lineage specific markers as shown in Table 2. By appropriate selection with particular factors and the development of bioassays which allow for self regeneration of stem cells and screening of the stem cells as to their markers, a composition enriched for viable stem cells may be produced for a variety of purposes.

The compositions enriched for stem cells may be used in hematopoietic engraftment, where the cells may be freed of neoplastic cells. Further, the use of autologous stem cells will avoid graft-versus-host disease. In addition, the cells may be modified by appropriate gene transfer recombination, either homologous or non-homologous, to correct genetic defects or provide genetic capabilities naturally lacking in the stem cells or their progeny, either as to the individual or as to hematopoietic cells generally. In addition, the stem cell Composition may be used to isolate and define factors associated with their regeneration and differentiation.

The cells obtained as described above may be used immediately or frozen at liquid nitrogen temperatures and stored for long periods of time, being thawed and capable of being reused. The cells will usually be stored in 10% DMSO, 50% FCS, 40% RPMI 1640 medium. Once thawed, the cells may be expanded by use of growth factors and/or stromal cells associated with stem cell proliferation and differentiation.

In another embodiment, the invention encompasses antibodies specific for the epitope recognized by HCC-1. The gene encoding CD59 has recently been isolated and its nucleotide sequence determined. Sawada et al. (1989) Nucl. Acids Res. 17:6728; Philbrick et al. (1990) Eur. J. Immunol. 20:87; Davies et al. (1989) J. Exp. Med. 170:637; and Okada et al. (1989) Biochem. Biophys. Res. Commun. 162:1553. Synthetic peptides corresponding to the epitope recognized by HCC-1 can be determined by detecting the specificity of HCC-1 to overlapping sets of synthetic peptides spanning the extracellular portion of CD59. Peptides specifically recognized by HCC-1 are used to raise additional antibodies, through techniques as described herein and well known to those skilled in the art. Alternatively, CD59 or cells expressing CD59 may be used to generate antibodies. The antibodies are then screened for their ability to either cómpete with HCC-1 or to bind specifically to the population of cells described herein.

As used herein, "HCC-1 antibodies" encompasses any antibody or fragment thereof, either native or recombinant, synthetic of naturally-derived, which retains sufficient specificity to bind specifically to the epitope that is recognized by HCC-1.

As used herein, HCC-1 means monoclonal antibody HCC-1 or any monoclonal antibody or polyclonal antibody, that binds to the epitope recognized by HCC-1 in such a manner as to recognize, preferentially, hematopdietic progenitor cells. This also includes any antibody having the same antigenic specificity as these antibodies.

The HCC-1 antibodies are obtained by methods known in the art for monoclonal antibody production, The actual mathods used are described in the Examples presented herein although any method known in the art of antibody production may be used. Such methods include, but are not limited to, separating B cells with cellsurface antibodies of the desired specificity, cloning the DNA expressing the variable regions of the light and heavy chains and expressing the recombinant genes in a suitable host cell. Standard monoclonal antibody generation techniques can be used wherein the antibodies are obtained from immortalized antibody-producing hybridoma cells. These hybridomas can be produced by immunizing animals with stem cells, purified CD59 protein or antigenic portions thereof, and fusing B lymphocytes from the immunized animals, preferably isolated from the immunized host spleen, with compatible, immortalized cells, preferably a B cell myeloma.

The invention further encompasses compositions of matter comprising the HCC-1 antibodies obtained by the methods described herein. As used herein, the terms "antibody" or "antibodies" include the entire antibody and antibody fragments containing functional portions thereof. The term "antibody" includes any monospecific or bispecific compound comprised of a sufficient portion of the light chain variable region and/or the heavy chain variable region to effect binding to the epitope to which the whole antibody has binding specificity. The fragments may include the variable region of at least one heavy or light chain, immunoglobulin polypeptide, and include, but are not limited to, Fab fragments, F(ab')$_2$ fragments, and Fv fragments.

In addition, the monospecific domains may be attached by any method known in the art to another suitable molecule. The attachment may be, for instance, chemical or by genetic engineering. The HCC-1 antibodies may be produced by any recombinant means known in the art. Such recombinane antibodies include, but are not limited to, fragments produced in bacteria and non-human antibodies in which the majority of the constant regions have been replaced by human antibody constant regions. In addition, such "humanized" antibodies may be obtained by host vertebrates genetically engineered to express the recombinant antibody.

The antibodies can be conjugated to other compounds including, but not limited to, enzymes, magnetic beads, colloidal magnetic beads, haptens, fluorochromes, metal compounds, radioactive compounds or drugs. The enzymes that can be conjugated to the antibodies include, but. are not limited to, alkaline phosphatase, peroxidase, urease and β-galactosidase. The fluorochromes that can be conjugated to the antibodies include, but are not limited to, fluorescein isothiocyanate, tetramethylrhodamine isothiocyanate, phycoerythrin, allophycbcyanins and Texas Red. For additional fluorochromes that can be conjugated to antibodies see Haugland, R. P. Molecular Probes: Handbook of Fluorescent Probes and Research Chemicals (1992–1994). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxigenin, oxazalone, and nitrophenol. The radioactive compounds that can be conjugated or incorporated into the antibodies are known to the art, and include but are not limited to technetium 99 m ($^{99}TC$), $^{125}I$ and amino acids comprising any radionuclides; including, but not limited to, $^{14}C$, $^{3}H$ and $^{35}S$.

In another embodiment, the present invention provides a method for obtaining compositions enriched for stem cells comprising isolating human hematopoietic cells which lack at least one lineage specific or non-specific marker (LIN$^-$) and express high levels of HCC-1. As used herein, HCC-1$^+$ or HCC-1$^{hi}$ cells refer to those cells in which the marker recognized by HCC-1antibodies is exposed to a high degree such that it is able to be bound by HCC-1 antibodies, or any other antibody that binds to the epitope recognized by HCC-1 antibodies. An example of a lineage non-specific marker is the 80 kD glycoprotein which appears to mask the HCC-1 epitope later in hematopoietic development. A highly enriched composition may be obtained by selective isolation of cellb that are CD34$^{+HCC-1hi}$ and LIN$^-$.

HCC-1$^+$ stem cells may be isolated from any known source of stem cells, including, but not limited to, bone marrow, both adult and fetal, mobilized peripheral blood (MPB) and.umbilical cord blood. Initially, bone marrow cells may be obtained from a source of bone marrow, including but not limited to, ilium (e.g. from the hip bone via the iliac crest), tibia, femora, spine, or other bone cavities. Other sources of stem cells include, but are not limited to, embryonic yolk sac, fetal liver, and fetal spleen.

For isolation of bone marrow, an appropriate solution may be used to flush the bone, including, but not limited to, salt solution, conveniently supplemented with fetal calf serum (FCS) or other naturally occurring factors, in conjunction with an acceptable buffer at low concentration, generally from about 5-25 mM. Convenient buffers include, but are not limited to, HEPES, phosphate buffers and lactate buffers. Otherwise bone marrow may be aspirated from the bone in accordance with conventional techniques.

Various techniques may be employed to separate the cells by initially removing cells of dedicated lineage. Monoclonal antibodies are particularly useful for identifying markers associated with particular cell lineages and/or stages of differentiation. The antibodies may be attached to a solid support to allow for crude separation. The separation techniques employed should maximize the retention of viability of the fraction to be collected. Various techniques of different efficacy may be employed to obtain "relatively crude" separations. Such separations are where up to 10%, usually not more than about 5%, preferably not more than about 1%, of the total cells present not having the marker may remain with the cell population to be retained. The particular technique employed will depend upon efficiency of separation, associated cytotoxicity, ease and speed of performance, and necessity for sophisticated equipment and/or technical skill.

Procedures for separation may include, but are not limited to, magnetic separation, using antibody-coated magnetic beads, affinity chromatography, cytotoxic agents joined to a monoclonal antibody or used in conjunction with a monoclonal antibody, including, but not limited to, complement and cytotoxins, and "panning" with antibody attached to a solid matrix, e.g., plate, elutriation or any other convenient technique.

The use of separation techniques include, but are not limited to, those based on differences in physical (density gradient centrifugation and counter-flow centrifugal elutriation), cell surface (lectin and antibody affinity), and vital staining properties (mitochondria-binding dye rho123 and DNA-binding dye Hoechst 33342).

Techniques providing accurate separation include, but are not limited to, FACS, which can have varying degrees of sophistication, e.g., a plurality of color channels, low angle and obtuse light scattering detecting channels, impedance channels, etc.

In a first separation, typically starting with about $1 \times 10^{8-9}$ preferably at about $5 \times 10^{8-9}$ cells, the HCC-1 antibody may be labeled with one fluorochrome, while the antibodies for the various dedicated lineages, or anti-gp80 antibodies, may be conjugated to at least one different fluorochrome. While each of the lineages may be separated in a separate step, desirably the lineages are separated at the same time as one is positively selecting for HCC-1 and/or other stem cell markers. The cells may be selected against dead cells, by employing dyes associated with dead cells (including but not limited to, propidium iodide (PI)). Preferably, the cells are collected in a medium comprising 2% FCS.

The purified stem cells have low side scatter and low to medium forward scatter profiles by FACS analysis. Cytospin preparations show the enriched stem cells to have a size between mature lymphoid cells and mature granulocytes. Cells may be selected based on light-scatter properties as well as their expression of various cell surface antigens.

While it is believed that the particular order of separation is not critical to this invention, the order indicated is preferred. Preferably, cells are initially separated by a coarse separation, followed by a fine separation, with positive selection for CD34 and HCC-$1^{hi}$.

Compositions having greater than 90%, usually greater than about 95% of CD34$^+$HCC-$1^{hi}$ cells may be achieved in this manner. The desired stem cells may be further enriched by selection for LIN$^-$ and/or Thy-$1^+$ and/or rho$^{lo}$, or combinations of these markers as listed in Table 2, and being able to provide for cell regeneration and development of members of all of the various hematopoietic lineages. Note that the blank spaces in Table 2 do not mean that the cells are negative for the specified marker; they simply mean the marker is not used.

TABLE 2

Possible Combinations of Selections for Stem Cell Populations

| HCC-$1^{hi}$ | CD34$^+$ | Thy$^+$ | LIN$^-$ | rho$^{lo}$ |
|---|---|---|---|---|
| + | + | + | + | + |
| + | + | + | + |   |
| + | + | + |   |   |
| + | + |   |   |   |
| + | + |   |   | + |
| + |   | + |   | + |
| + |   | + | + | + |
| + |   |   | + | + |
| + |   |   | + |   |
|   | + | + | + |   |
|   | + | + | + | + |
|   |   | + | + | + |
|   | + |   | + | + |
|   |   |   | + | + |

By separating CD34$^{+HCC-1hi}$ cells from human hematopoietic sources, the long-term culture activity is enriched in the HCC-$1^{hi}$ fraction compared to HCC-$1^{lo/-}$. Moreover, the HCC-$1^{hi}$ cells will generate both B and myeloid cells in long-term cultures. In further enrichments of the HCC-$1^{hi}$ cells using antibodies to Thy-1 and/or any of the combinations specified in Table 2 and/or c-kit, the stem cell frequency can be further increased.

The cells generated from CD34$^+$HCC-$1^{hi}$ cells and obtained from these cultures can give rise to B cells, T cells, erythroid cells and myelomonocytic cells in the in vivo assays described below.

Demonstration of sustained hematopoietic ability of the various cell populations might be accomplished by the detection of continued myeloid, erythroid and B-lymphoid cell production in the SCID-hu bone model. Kyoizumi et al. (1992) Blood 79:1704; Chen et al. (1994) Blood 84:2497. To analyze this potential, one may isolate human fetal bone and transfer a longitudinally sliced portion of this bone into the mammary fat pad of a scia/scid animal; the bone cavity is depleted of endogenous progenitor cells by whole body irradiation of the mouse host prior to injection of the test donor population. The HLA of the population which is injected is mismatched with the HLA of the recipient bone cells. Potent SCID-hu bone engrafting activity is found in the CD34$^+$HCC-$1^{hi}$ adult bone marrow cell population while none is detected in the CD34$^{+HCC-1lo/-}$ population. In one experiment which showed strong engraftment, it was possible to detect progeny of the myeloid, B-lymphocyte and erythroid lineages which derived from the CD34$^{+HCC-1hi}$ population (FIG. 11).

To demonstrate differentiation to T cells, fetal thymus is isolated and cultured from 4–7 days at about 25° C., so as to deplete substantially the lymphoid population. The cells to be tested for T cell activity are then microinjected into the thymus tissue, where the HLA of the population which is injected is mismatched with the HLA of the thymus cells. The thymus tissue may then be transplanted into a scid/scid mouse as described in U.S. Pat. No. 5,147,784, particularly transplanting under the kidney capsule.

Specifically, the sorted population of $CD34^+$ $HCC\text{-}1^{hi}$ cells can be microinjected into HLA mismatched thymus fragments. After 6–10 weeks, assays of the thymus fragments injected with $CD34^{+HCC\text{-}}1^{hi}$ cells can be performed and assessed for donor derived T cells. The majority, though not all, of SCID-hu thymus engrafting activity resides in the $CD34^{+HCC\text{-}}1^{hi}$ adult bone marrow population. A relatively small amount of thymus engrafting activity is observed in the $CD34^+HCC\text{-}1^{lo/-}$ population which was shown to be depleted of CAFC and SCID-hu bone engrafting activity (Table 9 and FIG. 10). This may indicate that the HCC-1 epitope is expressed at low levels on a T cell progenitor which is detectable in the SCID-hu thymus assay but which has no activity in the SCID-hu bone assay or CAFC assay. Subfractionation of the $CD34^{+HCC\text{-}}1^{hi}$ fraction based on. $Thy^+$ and/or c-kit and/or rho123 should demonstrate further enrichment of activity.

The subject cell compositions may find use in a variety of ways. They can be used to fully reconstitute an immunocompromised host such as an irradiated host and/or a host subject to chemotherapy; or as a source of cells for specific lineages, by providing for their maturation, proliferation and differentiation into one or more selected lineages by employing a variety of factors, including, but not limited to, erythropoietin, colony stimulating factors, e.g., GM-CSF, G-CSF, or M-CSF, interleukins, e.g., IL-1, -2, -3, -4, -5, -6, -7, -8, etc., or the like, or stromal cells associated with the stem cells becoming committed to a particular lineage, or with their proliferation, maturation and differentiation.

The $CD34^{+HCC\text{-}}1^{hi}$ cells may also be used in the isolation and evaluation of factors associated with the differentiation and maturation of hematopoieti, c cells. Thus, the $CD34^+$ $HCC\text{-}1^{hi}$ cells may be used in assays to determine the activity of media, such as conditioned media, evaluate fluids for cell growth activity, involvement with dedication of particular lineages, or the like.

The $CD34^{+HCC\text{-}}1^{hi}$ cells may be used for the treatment of genetic diseases. Genetic diseases associated with hematopoietic cells may be treated by genetic modification of autologous or allogeneic stem cells to correct the genetic defect. For example, diseases including, but not limited to, β-thalassemia sickle cell anemia, adenosine deaminase deficiency, recombinase deficiency, recombinase regulatory gene deficiency, etc. may be corrected by introduction of a wild-type gene into the $CD34^{+HCC\text{-}}1^{hi}$ cells, either by homologous or random recombination. Other indications of gene therapy are introduction of drug resistance genes to enable normal stem cells to have an advantage and be subject to selective pressure during chemotherapy. Suitable drug resistance genes include, but are not limited to, the gene encoding the multidrug resistance (MDR) protein.

Diseases other than those associated with hematopoietic cells may also be treated by genetic modification, where the disease is related to the lack of a particular secreted product including, but not limited to, hormones, enzymes, interferons, growth factors, or the like. By employing an appropriate regulatory initiation region, inducible production of the deficient protein may be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly hematolymphotropic diseases.

The following examples are offered by way of illustration and not by way of limitation.

EXAMPLE 1

Materials and Methods

Cell Preparations

Bone marrow (BM) aspirates were obtained from normal donors following informed consent. The cells were separated over lymphoprep (Nycomed Pharma As, Oslo, Norway) to obtain light density mononuclear cells (<1.077 g/dn). Mononuclear cells were obtained by selecting the interface cells, while granulocytes and erythrocytes were obtained from the pellet. Platelets were obtained by centrifuging peripheral blood (PB)-at 1000 rpm for 10 minutes, collecting the platelet-rich fraction and further centrifuging at 3000 rpm for 10 minutes. $CD34^+$ BM cells obtained using a fluorescence activated cell sorter were used for the immunization of BALB/c mice.

Cadaveric Bone Marrow and Mobilized Peripheral Blood

Cadaveric bone marrow cell suspensions derived from multi-organ donor vertebral bodies were obtained from Northwest Tissue Center (Seattle, Wash.). Patient peripheral blood samples were obtained after informed consent and chemotherapeutic regimens designed to mobilize primitive hematopoietic cells into the periphery. Multiple myeloma patients were mobilized with a high dose of cyclophosphamide and GM-CSF according to standard techniques. Typically, breast cancer patients were mobilized with a high dose of cyclophosphamide plus IL3 and G-CSF.

Cells were separated over IsoPrep harvesting the low density mononuclear cells (d<1.068 g/dL for cadaveric bone marrow, d<1.077 g/dL for peripheral blood) and were further processed for fluorescent activated cell sorting and analysis.

Production of Monoclonal Antibodies (MAbs)

BALB/c mice were immunized intrasplenically with $CD34^+$ BM cells, obtained as described above, in the presence of 20 μg muramyl dipeptide, per mouse, and boosted 3 times at 3 weekly intervals. Spleen cells were fused with the NSl-Ag 4-1 murine myeloma cell line using polyethylene glycol with selection of the hybridomas being performed in medium containing hypoxanthine-aminopterin-thymidine (HAT). Kohler and Milstein (1975) Nature, 256:495. The preliminary screens were performed to exclude antibodies that bound to T and B cell lines, and to mature cells. This was assessed by means of a peroxidase ELISA and indirect immunofluorescence. Supernatants that met this criteria were further screened for reactivity to primitive cells within the bone marrow. Primitive cells consisted of cells that did not express the CD18 antigen ($CD18^-$) and that did not agglutinate with soybean agglutinin ($SBA^-$). The resultant hybridoma supernatants that bound to this population were isotyped by means of a peroxidase ELISA and further screened for their reactivity with $CD34^+$ cells, by two color immunofluorescence, to identify antibodies that selected the cells expressing the CD34 antigen.

Hybridomas producing antibodies that were non-reactive with mature cells and bound to a small subpopulation of BM mononuclear cells (BMMNC), were cloned three times by limiting dilution and the isotype of the MAbs determined using a commercially available isotyping kit (Silenus, Australia). The HCC-1 MAb was found to be an IgM. Subsequent studies were performed using undiluted tissue culture supernatant.

Immunofluorescence Staining

Flow cytometric analysis of the reactivity of HCC-1 with various hematopoietic lineages within the BM and peripheral blood (PB) was performed using HCC-1 in combination with each of the following antibodies: CD2 (T11, Coulter, Hialeah, Fl.), CD3 (T3, Coulter), CD4 (T4, Coulter), CD7 (3A1, Coulter), CD8 (TS, Coulter), CD10 (CALLA, Becton Dickinson (BD), Mountain View, Ca.), CD13 (My7, Coulter), CD14. (TUK4, Dakopatts, A/S, Denmark), CD19 (HD37, Dako), CD20 (B1, Coulter), CD33. (LeuM9, BD), CD34 (8G12, BD), CD38 (Leu 17, BD), CD41a (Plt1, Coulter), CD45 (KC56, Coulter), CD71 (T9, Dako), HLA-Class Class 1 (W6/32, Dako), HLA-DR (L243, BD), GLY-A (JC159, Dako), c-kit (YB5.B8, Dr. L. Ashman, Hanson Center for Cancer Research, Adelaide, Australia) and WEMGl1 (Dr. A. Lopez, (I.M.V.S., Adelaide, Australia).

Antibody Staining For Fluorescent Activated Cell Sorting and Analysis

The buffer used in antibody staining was Dulbecco's modified phosphate buffered saline ($CA^{++}$ and $Mg^{++}$ free) supplemented with 2% fetal bovine serum, 10 mM HEPES, 10 U/mL heparin, and 1 mg/mL human gamma globulin (Gamimune, Miles)/ Cells were incubated at $10^7$/mL in HCC-1 hybridoma supernatant diluted ½ in buffer and anti-Thy1 antibody (GM201) at 5 µg/mL for 30 minutes on ice. Cells were washed and HCC-1 binding was detected by adding FITC-conjugated goat anti-mouse IgM and anti-Thy1 binding was detected by using PE-conjugated goat anti-mouse $IgG_1$ (both at 1/100 dilution, Southern Biotechnology Associates) and incubating for 30 minutes on ice. Cells were washed again and sulforhodamine conjugated anti-CD34 antibody (Tük 3) was added at 3 µg/mL and incubated 30 minutes on ice. Cells were washed and resuspended for cell sorting or analysis on a FACStar$^{PLUS}$ (Becton Dickinson, San Jose, Calif.) equipped with a dye laser (CR-599, Coherent, Palo Alto, Calif.) tuned to 600 nm to detect sulforhodamine fluorescence.

Dual color fluorescence was performed by simultaneously incubating undiluted HCC-1 supernatant with direct phycoerythrin (PE) conjugates of the monoclonal antibodies or a 1:1 mixture of their supernatants. Cells were incubated at 4° C. for 45 minutes, washed and further incubated for 45 minutes with a 1:50 dilution of goat anti-mouse IgM (µheavy chain-specific), conjugated to fluorescein isothiocyanate (FITC: Southern Biotechnology Associates, Birmingham, Al.). The IgG supernatants were detected using a 1:50 dilution of PE-conjugated goat anti-mouse IgG (γ heavy chain-specific; SBA, Birmingham, Al.). The CD41, CD71 and Glycophorin A monoclonal antibodies were FITC conjugated and thus HCC-1 was detected using goat anti-mouse IgM-PE. Analysis gates were set according to isotype matched control antibodies such that <1% cells were positive within that region. Unconjugated controls included supernatants of 3D3 (IgG1) and 1A6 (IgM), both anti-Salmonella antibodies (Dr. L. Ashman, Australia). Isotype matched controls conjugated with PE and FITC were obtained from Dakopatts. Flow cytometric analysis was performed using PROFILE II (Coulter Electronics, Hialeah, Fl.) with at least 50,000 events being collected in list mode.

The data was further analyzed using the EPICS-ELITE software. Cell sorting was performed on a FACStar$^{PLUS}$ (Becton Dickinson, Mountain View, Calif.). Sorted cells were collected into Iscoves Modified Dulbecco's Medium (IMDM) supplemented with 10% FCS.

Three color immunofluorescent labelling was performed by using an energy coupled dye (ECD), as the third fluorochrome. Bone,marrow cells were incubated simultaneously with hybridoma supernatant and two IgG isotype MAbs conjugated with FITC and PE. After washing, the cells were incubated with goat anti-mouse IgM conjugated to biotin (1/50 dilution, Southern Biotechnology) for 45 minutes on ice, washed 3 times and further incubated with a 1/50 dilution of streptavidin-ECD (Coulter). Once the immunolabelling was complete, the cells were fixed in 1% paraformaldehyde and analyzed using the Coulter Profile.

When the unconjugated antibodies YB5.B8 and HLA Class 1 were used, CD34 was detected with the ICH3 (IgG2a) antibody, followed by goat anti-mouse-IgG2a-PE (Caltag). YB5.B8 and HLA Class 1 were detected using goat anti-mouse-IgG1-FITC (Caltag).

Rhodamine 123 (Rh123)

Rh123 (Molecular Probes Inc., Portland, Oreg.) was stored at 1 mg/mL in PBS at −80° C. with a working solution used at 0.1 µg/mL in Hanks Balanced Salt Solution supplemented with 5% FCS (HBSS.5). BM cells were incubated at $10^7$/mL for 45 minutes at 37° C., 5% $CO_2$ and mixed every 15 minutes. They were washed twice in HBSS.5, resuspended in HBSS.5 and incubated for a further 15 minutes at 37° C. to remove residual unbound Rh123. The cells were washed twice more in HBSS.5 and then stained with antibodies labelled with PE and ECD. The cell samples containing Rh123 were not FACS fixed, as rhodamine is a vital dye, and were analyzed or sorted on the day of labelling.

Clonogenic Assays of Hematopoietic Progenitors

Sorted cell populations were assayed for their content of granulocyte macrophage colony forming cells (CFU-GM), primitive erythroid progenitors (BFU-E), and multipotential colony forming cell (CFU-GEMM). Cells were plated in triplicate at $10^3$ to $2\times10^4$ cells in 1 mL of medium consisting of 0.9% methyl cellulose in IMDM supplemented with 3 mM L-glutamine, 30% FCS, 1% deionized bovine serum albumin (BSA: Cohn fraction V, Sigma), 5% conditioned medium from the human bladder carcinoma cell line 5637, 1 ng rHu IL-3 (Amgen, Thousand Oaks, Calif.) and 4 U of rHu-erythropoietin (Eprex: 2000 units/mL, Janssen Cilag, Switzerland). All assays were incubated at 37° C. in a humidified atmosphere of 5% $CO_2$ in air. CFU-GM; BFU-E and CFU-GEMM colonies were scored on day 14 of culture according to standard criteria described by Simmons et al. (1990) *Proc. Natl. Acad. Sci. USA* 87:1386.

Long Term Bone Marrow Culture

This method is based on the methods described by Simmons and Torok-Storb (1991); *Blood*, 78:55; and Simmons et al. (1987) *Nature*, 328:429. BMMNC were cultured in T-25 tissue culture flasks (Corning) containing 10 mL long term liquid culture (LTLC) medium (α-minimal essential medium, Gibco) supplemented with folic acid (0.01 mg/mL), myoinositol (0.4 mg/mL, Sigma), 1 µM/L hydrocortisone sodium succinate (Sigma), $5\times10^{-5}$M beta mercaptoethanol, 12.5% FCS, and 12.5% horse serum (CSL, Melbourne, Australia), and maintained at 37° C. in 5% $CO_2$ for 3 to 4 weeks until the adherent layer of cells reached confluence. They were then irradiated at 15 Gy ($^{137}$Cs) and replated in LTLC medium at $1-2\times10^5$ cells per 35 mm tissue culture plate to be used as a source of stromal layers. $1\times10^4$ sorted BMMNC were resuspended in 3 mL LTLC and seeded onto each plate with each sorted fraction set up in triplicate. Clonogenic assays were also performed to provide numbers of input clonogenic cells in each of the fractions. At weekly intervals, over a period of up to 10 weeks, 1.5 mL of non-adherent cells were carefully removed from each culture and replaced with an equal volume of pre-warmed LTLC medium. The number of non-adherent cells present in the medium removed at each weekly feed was determined by counting, using a hemocytometer, and the number of clonogenic cells (CFU-GM, BFU-E) determined as described by Simmons et al. (1987) *Nature* 328:439; and Simmons et al. (1990).

Pre-CFU Assay

This assay was conducted as initially described by Iscove et al. (1989) *J. Immunol.* 142:2332 and modified by Haylock et al. (1992) *Blood* 80:1405. Immunolabelled BMMNC were sorted into cell fractions using the FACStar$^{PLUS}$ and resuspended into pre-CFU medium (IMDM supplemented with 30% FCS, 1% deionized BSA, 3 mM L-glutamine and $5\times10^{-5}$M beta mercaptoethanol) at a concentration of $10^3$ cells/mL. Triplicate 1 mL suspension cultures were established in 24 well plates in pre-CFU medium supplemented with each of the following human growth factors (HGF) at a final concentration of 10 ng/mL: human Interleukin-1β (IL-1β), IL-3, IL-6, granulocyte colony-stimulating factor (Q-CSF), granulocyte-macrophage colony stimulating factor (GM-CSF) and stem cell factor (SCF), all supplied by Amgen (Thousand Oaks, Calif.). Clonogenic assays were performed in triplicate to determine the number of CFU-GM in the input population of cells used to initiate the pre-CFU cultures. The cultures were incubated at 37° C. in 5% $CO_2$ for 28 days. At days 7, 14, 21 and 28, the contents of each,well were removed, washed in IMDM and cell counts performed to determine cell production over the previous week. One tenth of the harvested cells were assayed for their content of CFU-GM (as described above), and a further tenth set up in pre-CFU culture with fresh growth medium containing the 6 human growth factors mentioned above. The remainder of cells were used for immunophenotypic analysis or for the preparation of cytospins to assess cell morphology.

Leukemic Cells

Leukemic cells were obtained from patients and cryopreserved at −196° C., according to the method of To et al. (1989) *Bone Marrow Transplant* 4:41. Briefly, using sterile procedure, cells were suspended at $10^7$ to $10^8$ mL in RPMI and an equal volume of "freeze mix" (20% FCS and 10% dimethyl sulfoxide was added dropwise with shaking. The cell suspension was placed into 2 mL plastic cryo vials (Nunc Intermed, Denmark) and frozen in a controlled rate freezer (KRYO 10 series). Cryopreserved cells were rapidly diluted in pre-warmed (37° C.) medium for thawing cells ($Ca^{2+}$, $Mg2^+$-free HBSS supplemented with 10 mmol/L acid citrate, 2% BSA and 50 kunitz units/mL DNAase). This method was performed essentially as described by Haylock et al. (1992). Mononuclear cells were collected following separation over Lymphoprep, washed twice in thaw solution (above) and resuspended to $10^7$/mL for further analysis.

Cell Lines

Cell lines were maintained in sterile plastic flasks (75 cm² surface area, Corning 25110-75) in RPMI supplemented with 10% FCS at 37° C. in a humidified atmosphere containing 5% $CO_2$ in air. The TF-1 cell line was grown in medium supplemented with 10 ng/mL recombinant human GM-CSF (Amgen, Thousand Oaks, Calif.) and the MO7e cell line was supplemented with 10 ng/mL of rHu IL-3 (Amgen). All cell lines were subcultured, every 2 to 3 days, to maintain them in logarithmic phase of growth, between $5\times10^4$/mL and $5\times10^5$/mL. TF-1, MO7e, NALM-6 and RC2A cell lines were kindly provided by Dr. L. Ashman. All other hematopoietic cell lines (K562, HELDR, HEL900, HI-Meg, KG1, HL60, DAUDI, BALM, JURKAT, HUT78, MOLT4, and U937) are maintained routinely in the Matthew Roberts Laboratory, Hanson Centre for Cancer Research, IMVS, Adelaide, Australia.

EXAMPLE 2

Properties of Cells Recognized by HCC-1

The monoclonal antibody HCC-1 was selected primarily on the basis of its specificity for a subpopulation of $CD34^+$ cells in the bone marrow. The results presented in FIG. 1A show that a mean of 69.1 5.9% of $CD34^+$ cells in the bone marrow expressed HCC-1 (range 55–82%, n=5) compared to 46.4±9.5% of the $CD34^+$ cells in steady state peripheral blood (range 42 65%, n=3). The results presented in FIG. 1B indicate that the $CD34^{+HCC-}1^+$ and $CD34^{+HCC-}1^-$ subpopulations exhibited distinct light scatter properties, the former comprising cells with low right angled Light scatter and intermediate forward light scatter (FSC) while the $CD34^+$ HCC-$1^-$ population contained cells demonstrating a bimodal FSC distribution.

To characterize these two populations further, 3 color flow cytometric analysis was performed using HCC-1 and HPCA-2 (CD34) in combination with a panel of monoclonal antibodies of well defined specificity which identify lineage restricted antigens or activation markers. As shown in FIG. 2, HCC-1 bound to subpopulations of $CD34^+$ cells co-expressing myeloid (CD13, CD33), erythroid (glycophorin A), T lymphoid (CD2, CD7) and B lymphoid (CD10, CD19) restricted antigens. In FIG. 2, each of the contour plots were generated from a list mode file comprising some 200,000 events which were not subject to any gating parameter—i.e., scatter property or fluorescence intensity. Each of the histograms was generated from 10,000 $CD34^+$ events derived from the list mode file collected for each 3-color stained sample. As shown in Table 3, HCC-1 also subdivided the populations of $CD34^+$ cells expressing ckit, CD45, CD38 and HLA-DR.

In Table 3, data represent the mean±SD and range of 3–5 experiments for all lineage antigens except HLA-Class 1, CD71 and CD45 (for example, 57.2±5.0% of the $CD34^+$ $cD19^+$ cells express HCC-1).

TABLE 3

The Expression of HCC-1 by $CD34^+$ Committed Progenitors as Demonstrated by Fluorescence Activated Cell Sorting

| ANTIBODY | PERCENTAGE OF $CD34^+$ CELLS EXPRESSING LINEAGE ANTIGEN | PERCENTAGE OF $CD34^+HCC-1^+$ EXPRESSING LINEAGE ANTIGEN | PERCENTAGE OF CD34 LINEAGE ANTIGEN CELLS EXPRESSING HCC-1 |
|---|---|---|---|
| QUADRANT | 2, 4 | 2/ (1–2) | 2/ (2–4) |
| CD2 | 4.0 ± 0.9 (1.1–5.11) | 4.7 ± 1.0 (1.3–5.6) | 85.8 ± 6.2 (67–100) |

TABLE 3-continued

The Expression of HCC-1 by CD34+ Committed Progenitors as Demonstrated by Fluorescence Activated Cell Sorting

| ANTIBODY | PERCENTAGE OF CD34+ CELLS EXPRESSING LINEAGE ANTIGEN | PERCENTAGE OF CD34+HCC-1+ EXPRESSING LINEAGE ANTIGEN | PERCENTAGE OF CD34 LINEAGE ANTIGEN CELLS EXPRESSING HCC-1 |
|---|---|---|---|
| CD7 | 4.8 ± 1.4 (2.5–7.0) | 6.3 ± 2.2 (2.7–9.8) | 94 ± 3.8 (88–100) |
| CD10 | 23.4 ± 4.3 (17.3–29.5) | 15.7 ± 0.3 (15.3–16.0) | 51.2 ± 7.9 (40–62.4) |
| CD19 | 24.4 ± 4.7 (14–38.7) | 19.2 ± 3.8 (12.2–31.3) | 57.2 ± 5.0 (40.5–63.6) |
| CD13 | 14.8 ± 4.3 (6.1–25.6) | 13.0 ± 4.0 (5.2–23.1) | 60.1 ± 6.0 (50–84) |
| CD33 | 32.6 ± 3.6 (25.8–44.9) | 32.2 ± 3.7 (20.7–44.0) | 73.5 ± 7.1 (51.2–90.7) |
| GLY-A | 8.1 ± 0.0 (7.3–8.9) | 0.0 ± 1.2 (7.4–10.2) | 85.9 ± 4.2 (80.8–91) |
| CD38 | 91.6 ± 3.2 (80.8–97.7) | 86.9 41 2.6 (79.5–93.1) | 60.6 ± 4.6 (48.6–73.6) |
| HLA-DR | 86.7 ± 9.8 (62.3–99.1) | 81.0 ± 9.0 (63 – 96.6) | 62.2 ± 9.5 (45.4–78) |
| C-KIT | 52.4 ± 2.6 (49.2–55.5) | 61.0 ± 4.2 (55.8–66.1) | 97.3 ± 2.7 (84–90.5) |
| HLA-ABC | 99.3 | 97.8 | 73 |
| CD45 | 45 | 43.7 | 84.2 |
| CD71 | 95.4 | 60.6 | 74 |

HCC-1 expression is shown in FIGS. 12 and 13 and Table 4.

TABLE 4

HCC-1 EXPRESSION ON FICOLLED MOBILIZED PERIPHERAL BLOOD SAMPLE

| Sample # disease | % CD34+ | % HCC-1+ | % CD34+ cells that are HCC-1+ | % CD34+ cells that are thy+ | % CD34+ thy+ cells that are HCC-1+ |
|---|---|---|---|---|---|
| 133/1 multiple myeloma | 12 | 14 | 50 | 23 | 100 |
| 7446 breast cancer | 21 | 16 | 80 | 44 | 100 |
| 7650 breast cancer | 42 | 32 | 75 | 37 | 100 |

EXAMPLE 3

Reactivity of HCC-1 with Lineage Restricted Clonogenic Progenitors and Their Precursors As shown in Table 5, fluorescence activated cell sorting (FACS) of BMMNC consistently demonstrated that myeloid (CFU-GM) and erythroid (BFU-E) progenitors were recovered in both the CD34$^{+HCC-}$1$^+$ and CD34$^{+HCC-}$1$^-$ subpopulations.

TABLE 5

| EXPERIMENT | COLONIES/10³ CELLS | | |
|---|---|---|---|
| | CFU-GM | BFU-E | CFU-GEMM |
| 1 | | | |
| CD34+ | 18.5 ± 3.5 | 35 ± 7.1 | 0 |
| CD34+HCC-1+ | 30.7 ± 8.7 | 27 ± 9.5 | 0 |
| CD34+HCC-1− | 20.3 ± 5.5 | 30 ± 9.2 | 0 |
| 2 | | | |
| CD34+ | 69.5 ± 5.4 | 125 ± 15.0 | 0 |
| CD34+HCC-1+ | 70/3 ± 5.1 | 102 ± 15.7 | 0 |
| CD34+HCC-1− | 71.8 ± 6.2 | 180 ± 32.9 | 0 |
| 3 | | | |
| CD34+ | 105 ± 7.8 | 59.3 ± 9.10 | 0.7 ± 0.6 |
| CD34+HCC-1+ | 125 ± 8.5 | 27.0 ± 7.20 | 1.0 ± 1.0 |
| CD34+HCC-1− | 63.0 ± 10.1 | 62.7 ± 10.7 | 0 |
| 4 | | | |
| CD34+ | 57 ± 12.7 | 44.3 ± 12 | 0.7 ± 1.2 |
| CD34+HCC-1+ | 82 ± 12.7 | 34.5 ± 4.9 | 0.7 ± 0.6 |
| CD34+HCC-1− | 59 ± 3.60 | 50.0 ± 9.8 | 0 |

Data represent mean+SEM of three replicate cultures of four experiments.

The number of CFU-GM in the two subpopulations was not significantly different when compared with HCC-1+ and HCC-1− populations or with the incidence of CFU-GM in the unfractionated CD34+ population (Fridman two-way analysis of variance p<0.05)). However, for BFU-E there was a trend towards high numbers in the HCC-1− subpopulation although this did not reach statistical significance. In addition, the BFU-E in the CD34$^{+HCC-}$1$^+$ fraction were mainly of the large multicentric.type while those in the HCC-1− fraction were smaller colonies comprising either single erythroid colonies or small clusters. In contrast to the presence of lineage restricted progenitors in both HCC-1+ and HCC-1− subpopulations, multipotential clonogenic cells (CFUGEMM) were recovered only in the CD34+ HCC-1+ population.

The presence of hierarchically more primitive progenitors in the CD34$^{+HCC-}$1$^+$ and CD34$^{+HCC-}$1$^-$ subpopulations was also examined. Previous studies have shown that primitive hematopoietic cells with the capacity to initiate and maintain hematopoiesis in standard stromal-cell-dependent long term marrow. culture conditions (Long-term culture-initiating cells; LTC-IC, Sutherland et al. (1989) *Blood* 74:1563.) or in cytokine driven suspension culture assays (pre-CFU assay, Smith et al. (1991) Blood 77:2122; and Brandt et al. (1990) *J. Clin. Invest.* 86:932) are small blasts exhibiting high levels of the CD34 antigen but low to undetectable levels of CD33, CD38 or HLA-DR and low retention of the vital fluorescent dye Rhodamine 123. Andrews et al. (1989); Tershappen et al. (1991); Brandt et al. (1990); and Udomsakdi et al. (1991). The high level of HCC-1 on CD34+ cells lacking expression of these antigens and on CD34$^{+Rho1°}$ cells (as shown in FIG. 2) suggested the likelihood that LTC-IC and pre-CFU would be present in the subpopulation of CD34+ cells whfch bound HCC-1. Accordingly, CD34+ $_{HCC-}$1$^+$and CD34$^{+HCC-}$1$^-$ fractions were isolated from normal adult BMMNC and assayed for their ability to initiate hematopoiesis following co-culture in LTBMC with irradiated allogeneic marrow stromal cells. As shown in FIG. 3, cells with the capacity to sustain the production of CFU-GM and mature myeloid cells were present only in the CD34+ $_{HCC-}$1$^+$ population.

Udomsakdi et al. (1991) presented data demonstrating low retention of Rho123 by CD34+ cells with similar in vitro potential (i.e., LTC-IC). Accordingly, three color FACS was employed to subdivide the CD34$^{+Rholo}$ population into HCC-1$^+$ and HCC-1$^-$ fractions. FIG. 2 illustrates that 8.5% of the CD34$^+$ cells were Rho$^{lo}$HCC-1$^-$. The while 1.5% of the CD34$^+$ cells were Rho$^{lo}$HCC-1$^-$. The experiments shown in FIG. 3 demonstrated that primitive hematopoietic cell activity was restricted to the, subpopulation of CD34$^+$ $_{Rho}{}^{lo}$ cells which bound the HCC-1 antibody (i.e. CD34$^+$ $_{Rho}{}^{lo}$HCC-1$^+$).

A similar series of experiments was performed to assess the capacity of the CD34$^{+HCC-}$1$^+$ and CD34$^{+HCC-}$1$^-$ subpopulations for de novo generation of CFU-GM in cytokine-driven stromal cell-free suspension culture (pre-CFU) assay (Smith, et al. (1991); Brandt, et al. (1990); Haylock, et al.). FIG. 5 shows that, in accord with the results obtained in the stromal cell dependent assay, only CD34$^{+HCC-}$1$^+$ cells sustained the production of CFU-GM in pre-CFU culture conditions. The CD34$^{+HCC-}$1$^+$ population was further subdivided into CD34$^{+HCC-}$1$^{hi}$ and CD34$^{+HCC-}$1$^{lo}$, as shown in FIG. 4. Analysis of the differentiative capacity of these two subsets, shown in FIG. 5, demonstrated that cells with the capacity for de novo generation of CFU-GM were restricted almost entirely to the CD34$^{+HCC-}$1$^{hi}$ subpopulation.

EXAMPLE 4

Expression of the HCC-1 Antigen on CD34$^+$

Hematopoietic Cells

Figure 6:
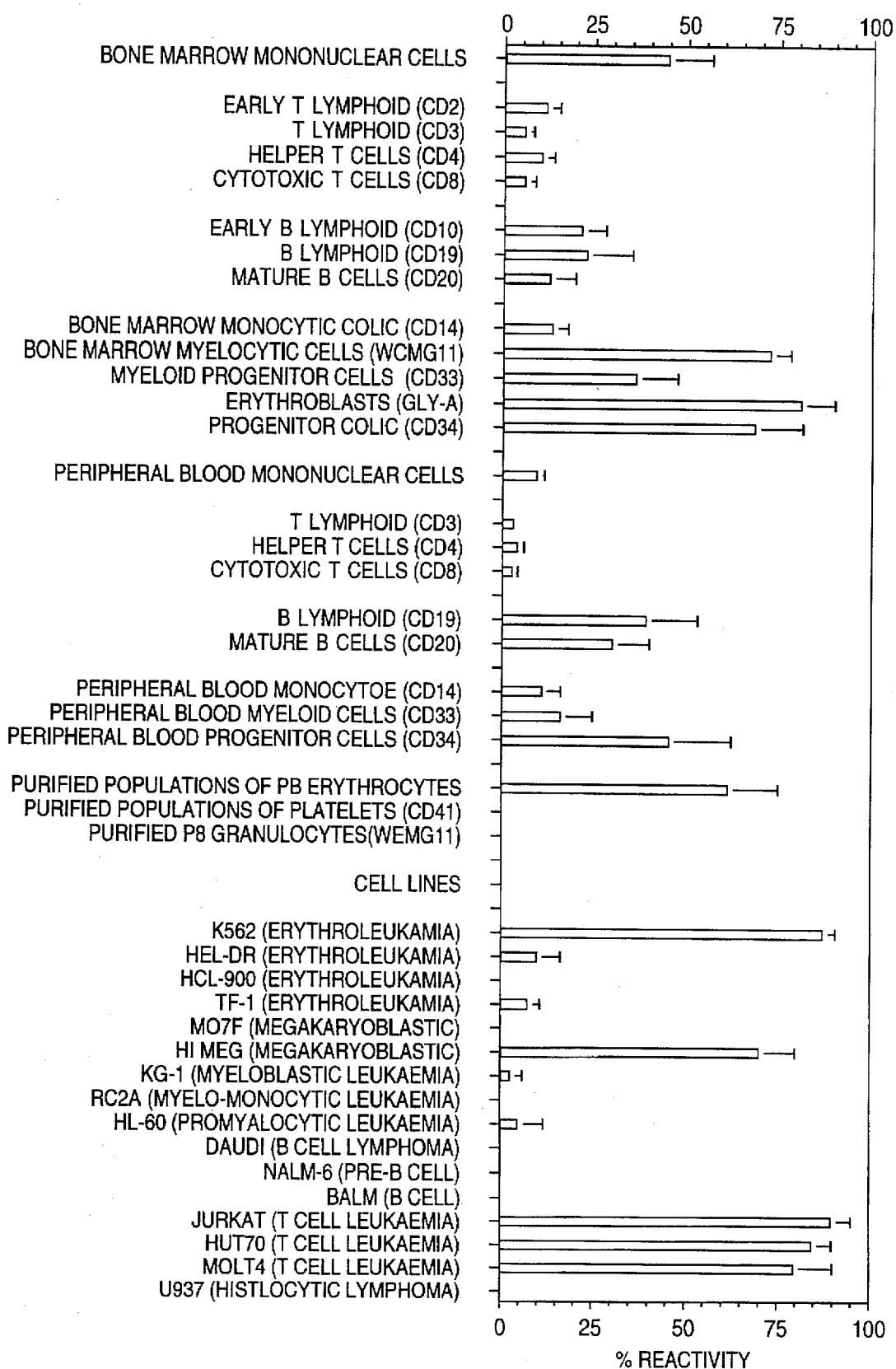
FIG. 6. HCC-1 expression by various hematopoietic cells and cell lines. Data represent the mean±SD of 4 samples for bone marrow cells and 3 samples for peripheral blood cells. Analysis of HCC-1 expression on cell lines was performed at least twice per cell line.

The HCC-1 monoclonal antibody was examined for its reactivity on normal human bone marrow (BMMNd) and peripheral blood mononuclear cells (pBMNC) by indirect immunofluorescence, as shown in FIG. 6. In 8 normal individuals HCC-1 was expressed on 45.9±4.1% (mean±SEM, n=8) BMMNC while in the peripheral blood. HCC-1 was expressed on 9.8±2.2% (mean±SEM, n=6).

HCC-1 was found to be expressed on a minor proportion of T lymphoid cells in the BM (12±2.0% of CD2$^+$ cells expressed HCC-1) while a greater proportion (23.9±6.4%) of CD19$^+$ B lymphoid cells expressed HCC-1. 37.4±5.7% of the CD33$^+$ myeloid cells in the BM expressed HCC-1, while mature granulocytes found in the PB did not express the antigen. HCC-1 was not detectable on purified populations of platelets but was detected on 61.9±6.7% (n=4) of erythrocytes as determined by co-expression with the erythroid specific antigen, glycophorin A (GLY-A).

EXAMPLE 5

Expression of the HCC-1 Antigen on Cell Lines

The expression of HCC-1 on a variety of cultured hematopoietic cell lines was tested by indirect immunofluorescence. Cell lines were immunolabeled with HCC at 4° C. for 45 minutes, washed and further incubated for 45 minutes with a 1:50 dilution of goat antimouse IgM (μ chain specific) conjugated to phycoerythrin (PE, Southern Biotechnology Associates, Birmingham, Ala.). After washing twice in HBSS5, the cells were fixed using 1% paraformaldehyde and subjected to flow cytometric analysis using a Profile II (Coulter, Hialeah, Fl.). Analysis gates were set according to a non-binding isotype matched IgM control antibody 1A6 (Dr. Leohie Ashman, Hanson Center for Cancer Research, IMVS). The results obtained are depicted in FIG. 6 and illustrate that HCC-1 did not bind to B cell lines nor the histiocytic cell line U937 while the T cell lines and K562 all expressed high levels of the HCC-1 antigen.

EXAMPLE 6

Expression of HCC-1 on Human Leukemic Cells

As HCC-1 was expressed on the majority of BMMNC that expressed CD34 and CD33 it was of interest to determine whether leukemic cells also expressed HCC-1. In each case the diagnosis was established by standard clinical criteria and extensive characterization of cell surface markers. Bone marrow samples were obtained at the time of diagnosis and tested for expression of CD34 and HCC-1. Representative examples are shown in FIG. 7 and the data are summarized in Table 6.

TABLE 6A

Reactivity of HCC-1 with Leukemic BM

| PATIENT UPN NO. | SUB-TYPE | TOTAL CD34 % | TOTAL HCC-1 % | % OF CELLS CO-EXPRESSING HCC-1 AND CD34 | % OF CD34 CELLS EXPRESSING HCC-1 |
|---|---|---|---|---|---|
| QUADRANT | | 2 + 4 | 1 + 2 | 2 | 2/(2 + 4) |
| NORMAL (Range) | | 3.8 ± 0.5 (2.2–4.9) | 45.5 ± 4.2 (33–55) | 2.6 ± 0.5 (1.65–4.0) | 69.1 ± 5.9 (55–82) |
| AML | | | | | |
| 1132 | M1 | 94.6 | 0.5 | 0.3 | 0.3 |
| 1366 | M1 | 17.5 | 3.7 | 1.4 | 8 |
| 505 | M1 | 28.2 | 17.3 | 2.2 | 7.8 |
| 954 | M1 | 64.5 | 13.6 | 9.5 | 14.7 |
| 1205 | M1 | 78.9 | 86.5 | 75.2 | 95.3 |
| 931 | M1 | 75.1 | 76.1 | 63.1 | 84 |
| 378 | M1 | 0 | 73 | 0 | 0 |
| 1558 | M1 | 96.6 | 1.3 | 0.4 | 0.4 |
| 1574 | M2 | 78.5 | 4.6 | 1.8 | 2.3 |
| 1695 | M2 | 93.6 | 60 | 55.9 | 59.7 |
| 842 | M2 | 77.7 | 9.8 | 4 | 5 |
| 947 | M2 | 86.5 | 4 | 0.3 | 0.3 |
| 864 | M2 | 92.7 | 2 | 1.1 | 1.2 |
| 253 | M2 | 45.4 | 0.9 | 0.7 | 1.5 |
| 617 | M2 | 86.6 | 1.9 | 0.9 | 1 |
| 940 | M2 | 79.1 | 16 | 9.4 | 11.9 |
| 1461 | M2 | 63.7 | 73 | 43 | 67.5 |
| 545 | M2 | 44.8 | 55.1 | 33.4 | 74.6 |
| 1216 | M2 | 4.2 | 81.6 | 0.4 | 9.5 |
| 840 | M4 | 64.6 | 1.1 | 0.6 | 0.9 |
| 595 | M4 | 44.7 | 1.7 | 1.2 | 2.7 |
| 665 | M4 | 8.2 | 1.1 | 0.1 | 1.2 |
| 784 | M4 | 0.9 | 46.9 | 0.8 | 88.9 |
| 1508 | M4 | 65.9 | 56.9 | 46.4 | 70.4 |
| 1412 | M4 | 82.1 | 21 | 15.8 | 19.2 |
| 1580 | M4 | 4.4 | 3.7 | 0.1 | 2.3 |
| 1822 | M4 | 1 | 14 | 0.1 | 10 |
| 978 | M5 | 0.2 | 11.3 | 0.2 | 100 |

TABLE 6B

Reactivity of HCC-1 with Leukemic BM

| PATIENT UPN No. | TOTAL CD34 % | TOTAL HCC-1 % | % OF CELLS COEXPRESSING HCC-1 AND CD34 | % OF CD34 CELLS EXPRESSING HCC-1 |
|---|---|---|---|---|
| QUADRANT | 2 + 4 | 1 + 2 | 2 | 2/(2 + 4) |
| NORMAL (Range) | 3.8 ± 0.5 (2.2–4.9) | 45.5 ± 4.2 (33–55) | 2.6 ± 0.5 (1.65–4.0) | 69.1 ± 5.9 (55–82) |
| ALL | | | | |
| 1231 | 6/.2 | 1 | 0.3 | 0.1 |

TABLE 6B-continued

Reactivity of HCC-1 with Leukemic BM

| PATIENT UPN No. | TOTAL CD34 % | TOTAL HCC-1 % | % OF CELLS COEX-PRESSING HCC-1 AND CD34 | % OF CD34 CELLS EXPRESSING HCC-1 |
|---|---|---|---|---|
| 697 | 75.9 | 4.4 | 2.2 | 2.9 |
| 1215 | 97 | 11.1 | 9.9 | 10.2 |
| 1248 | 24.5 | 1.3 | 0.1 | 0.4 |
| 810 | 51.4 | 1.9 | 1.4 | 2.7 |
| 1710 | 67.8 | 5.6 | 3.1 | 4.5 |
| UN-CLASSIFIED ACUTE LEUK. | | | | |
| 823 | 51.5 | 0.8 | 0.3 | 0.6 |
| 46 | 80.1 | 1.4 | 0.8 | 1 |
| 628 | 34.4 | 20.1 | 2.4 | 7 |
| 1558 | 96.6 | 1.8 | 0.5 | 0.5 |
| 630 | 79 | 15.8 | 11 | 13.9 |
| CML | | | | |
| 358 | 31.8 | 17.2 | 7.9 | 24.8 |
| 678 | 19.1 | 31.3 | 6.7 | 35.1 |
| 738 | 1.8 | 86.4 | 1.3 | 72.2 |
| 412 | 22.9 | 7.5 | 2.9 | 12.7 |
| 1045 | 4.5 | 63.4 | 2.5 | 55.6 |
| 846 | 7.2 | 51.7 | 3.8 | 52.8 |
| 692 | 53.5 | 28.4 | 10.4 | 19.4 |
| 748 | 5.9 | 76.6 | 5.2 | 88.1 |
| 1013 | 96 | 80.8 | 79.3 | 82.6 |
| 487 | 9.9 | 44.7 | 9 | 90.9 |
| 1507 | 12.3 | 16.6 | 4 | 32.5 |
| 800 | 35.2 | 49.7 | 24.1 | 68.5 |
| 858 | 9.8 | 43.8 | 3.9 | 39.8 |
| 335 | 6.2 | 23.4 | 4.6 | 74.2 |
| 1458 | 31.6 | 50.9 | 21.7 | 68.7 |
| 793 | 5.4 | 26.1 | 2.4 | 44.4 |
| 1722 | 26.1 | 40 | 7.2 | 27.6 |

HCC-1 was found to be expressed on all leukemic samples analyzed, although 77% of acute leukemics expressed below normal levels of HCC-1. The expression of the CD34 antigen on acute leukemic BM cells was increased in 87% of samples. However, the expression of HCC-1 on CD34$^+$ cells was decreased in 80% of the acute leukemic samples. Chronic myeloid leukemic (CML) samples were also tested for their expression of HCC-1. A greater proportion of CML samples expressed a higher percentage of HCC-1 on CD34$^+$ cells than that seen in the acute leukemic samples tested.

EXAMPLE 7

Cloning CD59

To isolate the gene encoding the HCC-1 antigen, a retroviral expression library was constructed by the method of Rayher and Gonda (Mol. Cell Biol. 1994), using mRNA from primary stromal cell cultures. cDNA transcripts were directionally cloned into the retroviral plasmid vector pRUF.neo. DNA from the library was used to transfect an amphotropic packaging cell line and transiently generated retroviral particles were harvested and used to stably infect an ecotropic packaging cell line. Virus produced from the latter cells was subsequently used to infect the factor-dependent murine hematopoietic cell line FDC-P1.

Infected FDC-P1 cells were selected for G418 resistance, and then cells expressing the HCC-1 antigen were isolated and enriched. Clonal populations of the transfectants were established following FACS sorting and colony isolation in methylcellulose.

To isolate the cDNA insert from the proviral integrant, PCR amplification was utilized. Following this, the cDNA was sequenced and Genbahk/EMBL sequence homology search revealed that mAbHCC-1 recognized the antigen encoded by the human lymphocyte antigen (CD59) gene. To confirm this result, the CD59 cDNA was subcloned into pRUF.neo and ultimately used to infect FDC-P1 cells as described above. In addition to HCC-1, an independent anti-CD59 MAb (MEM 43) was able to bind to the CD59-expressing transfectant.

EXAMPLE 8

Separation of bone Warrow cells. into HCC-1$^{hi}$ and HCC-1$^{lo}$ populations

Figure 8A:
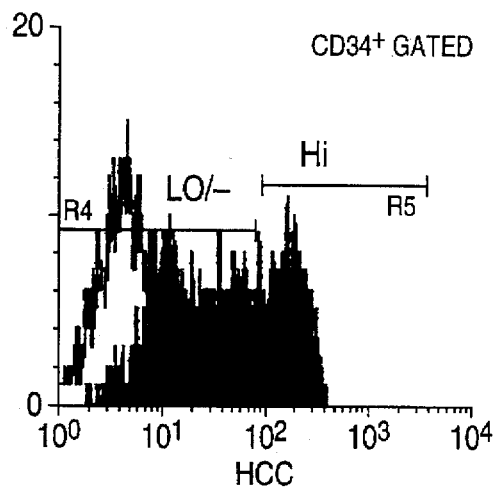
Figure 8B:
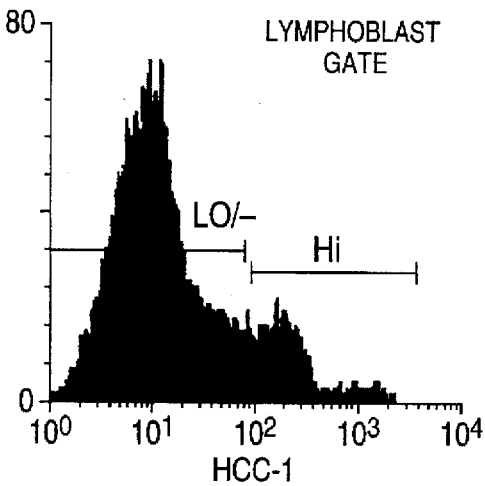

Cadaveric bone marrow cells were obtained, processed and stained with HCC-1 and antibodies to CD34 and Thy-1 as described in Example 1. CD34$^+$ cells sorted for HCC-1 staining were found to form two distinct populations designated MCC-1$^{lo/-}$ and HCC-1$^{hi}$. FIG. 8A. HCC-1$^{hi}$ cells typically had a mean fluorescence intensity of greater than 10 times that of an isotype control antibody. HCC-1$^{hi}$ cells were found to be in the minority of the cells obtained. FIG. 8B. The HCC-1$^{lo/-}$ cells (FIG. 8C) were found to be largely (74%) Thy-1$^-$CD34$^-$ and only 2.5% Thy-1$^+$CD34$^+$ (FIG. 8D); whereas the HCC-1$^{hi}$ cells (FIG. 8E) were found to be 31% Thy-1$^+$CD34$^+$ and 30% Thy-1$^-$CD34$^-$ (FIG. 8F).

EXAMPLE 9

Characterization of HCC-1$^+$ Cells

Sorted cell populations were analyzed by limiting dilution analysis for cobblestone area forming cell frequency at 3–6 weeks of coculture on stromal cells by limiting dilution analysis according to the method described by Baum et al. (1989) with the addition of human recombinant IL-6 10 ng/mL and LIF 20 ng/mL to enhance the proliferation of adult bone marrow cells.

A murine stromal cell line, AC6, described in Whitlock et al. (1987) Cell 48:1009–1021, serves as the supportive environment. A passage of AC6, AC6.21, is used herein and is alternatively referred to as Sys1. Confluent stromal cell layers were maintained for up to 7–8 weeks without passage by changing of the tissue culture medium every 5–7 days. To passage, the stromal cell layers were washed 3 times with serum-free medium, then overlaid with 2.5 mL (T-25 flask) of 0.5 mg/mL collagenase-dispase (Boehringer-Mannheim, Indianapolis, Ind.) in serum-free medium. The cultures were allowed to incubate 15–30 minutes at 37° C.; then the cells in the enzyme-containing medium were collected and RPMI-1640 medium with serum added. The stromal cells were suspended by pipetting with a Pasteur pipette, then cultured directly at ⅕th to ⅕₀th the original cell concentration. In general, confluent stromal layers subcultured at 1:10 reached confluency again after 5–7 days.

CD34$^+$ cadaveric bone marrow cells sorted into HCC-1$^{hi}$ and HCC-1$^{lo/-}$ subsets were cultured at limiting dilutions on a pre-established stromal cell monolayer (AC6.21) under conditions favoring hematopoietic development. (50% IMDM, 45% RPMI, 5% fetal calf serum, supplemented with 50 μM 2-mercaptoethanol, 1 mM sodium pyruvate, 100 U/mL penicillin, 100 μg/mL streptomycin, 4 mM L-glutamine, 10 ng/mL human recombinant IL-6 and 20 ng/mL human recombinant LIF). Cultures were visually scored for the presence of tightly formed clusters of non-refractile cells (cobblestone areas). Cultures were scored weekly for the presence of cobblestone areas of 50 cells and the frequency of cobblestone area forming cells (CAFC) initially plated was calculated by limiting dilution analysis.

The emergence of both myeloid and B lymphoid progeny was determined after 6 weeks by harvesting cells from culture plates and staining with anti-CD19-FITC, anti-CD15-FITC and anti-CD33-PE (all from Becton Dickinson) and analyzing on the FACSCAN. The results obtained are presented in FIG. 9 and Table 7.

TABLE 7

AC6.21 COCULTURE SUMMARY

| Population | Week 6 Frequency |
|---|---|
| HCC-1 hi/CD34+ | 1/41–1/94 |
| HCC-1 lo/CD34+ | 1/528–1/2067 |
| CD34+ | 1/64–1/264 |

EXAMPLE 10

SCID-hu Thymus Assay

Sorted cell populations were microinjected into fetal thymic pieces and implanted under the kidney capsule of scid/scid mice according to the method described by Galy et al. (1994) Blood 84:104. Six weeks after implantation, thymic pieces were recovered and analyzed for the presence of T cell progeny. Briefly, fragments of fetal thymus were placed on nitrocellulose filters (0.8 μm, Costar Corp., Cambridge, Mass.) on top of gelatin rafts (Gelfoam, Upjohn) according to the method described by Galy et al. (1993) J. Exp. Med. 178:391. After 7–13 days of incubation at 25° C. and 5% $CO_2$, thymus fragments were irradiated with 250 cGy from a $^{137}Cs$ source (J. L. Shepherd & Associates), washed and immediately micro-injected with the CD34+ cadaveric bone marrow cells sorted into HCC-1$^{hi}$ or HCC-1$^{lo/-}$ subsets of HLA-mismatched sorted cells in a 1 μl volume using an oil-filled micro-injector (Narishige) and 1 mm diameter glass micropipettes (World Precision Instruments). Fragments were placed back on the filters and incubated at 37° C., 5% $CO_2$ overnight and then inserted under the kidney capsule of anesthetized 6–8 week old scid/scid mice bred at SyStemix, Inc. (Palo Alto, Calif.). Mice were sacrificed 6 weeks after transplantation and the thymus grafts were recovered, reduced to a single cell suspension, and subjected to three-color immunofluorescence analysis on the FACScan. The following MAbs were used: fluorescein-conjugated anti-HLA antibodies, anti-CD2 or mouse IgG1 irrelevant control, phycoerythrin-conjugated W6/32, anti-CD1a (Coulter), anti-CD4 or mouse IgG1 control (Becton Dickinson) and Tricolor (TC)-conjugated anti-CD45, -CD8, -CD3 or mouse IgG1 irrelevant control (Caltag). Results are presented in FIG. 10, where "positive" indicates grafts with >1% donor-derived thymocytes.

EXAMPLE 11

SCID-hu Bone Assay

Sorted cell populations were injected into fetal bone pieces that had been implanted subcutaneously into scid/scid mice according to the method described by Chen et al. (1994) Blood 84:2487. Eight weeks after injection the bone grafts were analyzed for myeloid, erythroid, and lymphoid progeny. Briefly, split fetal long bones were implanted subcutaneously into the mammary fat pads of SCID mice under anesthesia. HLA immunophenotyping of the recipient fetal bone and of donor ABM cells was performed with FITC-conjugated MA2.1, BB7.2, GAP-A3 and W6/32 MAbs derived from hybridomas obtained from the American Type Culture Collection (ATCC). SCID-hu bone mice were used as recipients for CD34+ cadaveric bone marrow cells sorted into HCC-1$^{hi}$ and HCC-1$^{lo/-}$ subsets of HLA-mismatched sorted cell populations 8 weeks post-bone implantation and were conditioned by receiving a single whole body irradiation dose (400 cGy from a $^{137}Cs$ source, Gamma Cell 40, J. L. Shepherd & Associates). Sorted cells (3×10$^4$ in 10 μL) were then injected directly into the transplanted bone using a needle attached to a Hamilton syringe. After 8 weeks, mice were sacrificed and human bones were removed. Flushed bone cells were resuspended into a red blood cell lysing solution, then washed twice in buffer and counted before being stained with FITC conjugates of HLA antibodies while the various hematopoietic lineages were detected with PE-conjugated antibodies: anti-CD19 and anti-CD20 (B cells); anti-CD33, anti-CD14, and anti-CD15 (myeloid cells); anti-CD16 and anti-CD56 (NK cells); anti-glycophorin A (erythroid cells); and anti-CD34 (progenitor cells). FITC and PE-conjugated irrelevant mouse immunoglobulins were used as negative controls. Cells were analyzed on a FACScan fluorescent cell analyzer (Becton Dickinson). The results are presented in FIG. 11, where "positive" indicates grafts with donor-derived cells and Table 8. The results show that the CD34$^{+HCC-1hi}$ population contains all of the SCID-hu bone engrafting potential and that it gives rise to cell, myeloia, NK, erythroid and CD34+ progenitor cells

TABLE 8

SCID-hu BONE SUMMARY

| Population | Number Grafts Showing Donor Cell Engraftment |
|---|---|
| HCC-1 hi/CD34+ | 11/11 |
| HCC-1 lo/CD34+ | 0/13 |
| CD34+ | 8/8 |

Although the foregoing invention has been described in some detail byway of illustration and example for purposes of clarity of understanding, it will be apparent to those skilled in the art that certain changes and modifications may be practiced. Therefore, the description and examples should not be construed as limiting the scope of the invention, which is delineated by the appended claims.

What is claimed is:

1. A method of obtaining a composition substantially enriched in subpopulation of hematopoiefic stem cells comprising:

(a) obtaining, a source of cells comprising human hematopoietic cells;

(b) isolating a population of human hematopoietic cells from the source;

(c) contacting the population of human hematopoietic cells with a monoclonal antibody specific for the marker HCC-1; and (d) separating the subpopulation that is specifically bound by the monoclonal antibody, thereby obtaining a composition substantially enriched in a subpopulation of human hematopoietic stem cells.

2. The method according to claim 1 wherein the step of isolating a population of hematopoietic cells is by selecting the cells for expression of at least one additional marker associated with stem cells or by physical separation means.

3. The method according to claim 2 wherein the additional marker is selected from the group consisting of CD34, Thy-1$^+$, rho$^l$, and C-Kit$^+$.

4. A composition comprising a substantially enriched subpopulation of cells expressing HCC-1 obtained by the method according to claim 3.

5. A composition comprising a substantially enriched subpopulation of cells expressing HCC-1 obtained by the method according to claim 2.

6. A composition comprising a substantially enriched subpopulation of cells expressing HCC-1 obtained by the method according to claim 1.

7. The method according to claim 1 wherein the step of isolating a population of hematopoietic cells is by selecting cells for the absence of at least one lineage specific (LIN$^-$) marker.

8. The method according to claim 7 wherein the lineage specific marker is selected from the group consisting of CD14 and CD15, CD38, HLA-DR, CD71, and CD33.

9. A composition comprising a substantially enriched Subpopulation of cells expressing HCC-1 obtained by the method according to claim 8.

10. The method according to claim 7 wherein the lineage specific marker is selected from the group consisting of CD2, CD16, CD19, and glycophorin A.

11. A composition comprising a substantially enriched subpopulation of cell's expressing HCC-1 obtained by the method according to claim 5.

12. A composition comprising a substantially enriched subpopulation of cells expressing HCC-1 obtained by the method according to claim 7.

13. The method according to claim 7 wherein the step of isolating a population of human hematopoietic cells further comprises selecting the cells for the expression of at least one additional marker associated with stem cells.

14. A composition comprising a substantially enriched subpopulation of cells expressing HCC-1 obtained by the method according to claim 13.

15. The method according to claim 13 wherein the additional marker is selected from the group consisting of CD34, Thy-1$^+$, rho$^{lo}$ and C-Kit$^+$.

16. A composition comprising a substantially enriched subpopulation of cells expressing HCC-1 obtained by the method according to claim 15.

17. The method according to claim 13 whereto the lineage specific marker is selected from the group consisting of CD14, CD15, CD38, HLA-DR, CD71 and CD33.

18. A composition comprising a substantially enriched subpopulation of cells expressing HCC-1 obtained by the method according to claim 17.

19. The method according to claim 13 wherein the lineage specific marker is selected from the group consisting of CD2, CD16, CD19 and glycophorin A.

20. A composition comprising a substantially enriched subpopulation of cells expressing HCC-1 obtained by the method according to claim 19.

21. The method according to claim 1, where, step (c) is performed prior to step (b).

22. The composition substantially enriched in a subpopulation of hematopoietic stem cells obtained by the method of claim 21.

23. The hybridoma cell line designated ATCC Accession No. HB 11729.

24. The monoclonal antibody produced by the hybridoma cell line of claim 23.

25. An antibody that specifically binds to the epitiope that is specifically bound by the monoclonal antibody of claim 24.

26. A fragment of the antibody of claim 24 that includes the variable region of at least one heavy or light chain.

* * * * *

UNITED STATES PATENT AND TRADEMARK OFFICE

CERTIFICATE OF CORRECTION

Figure 5A:
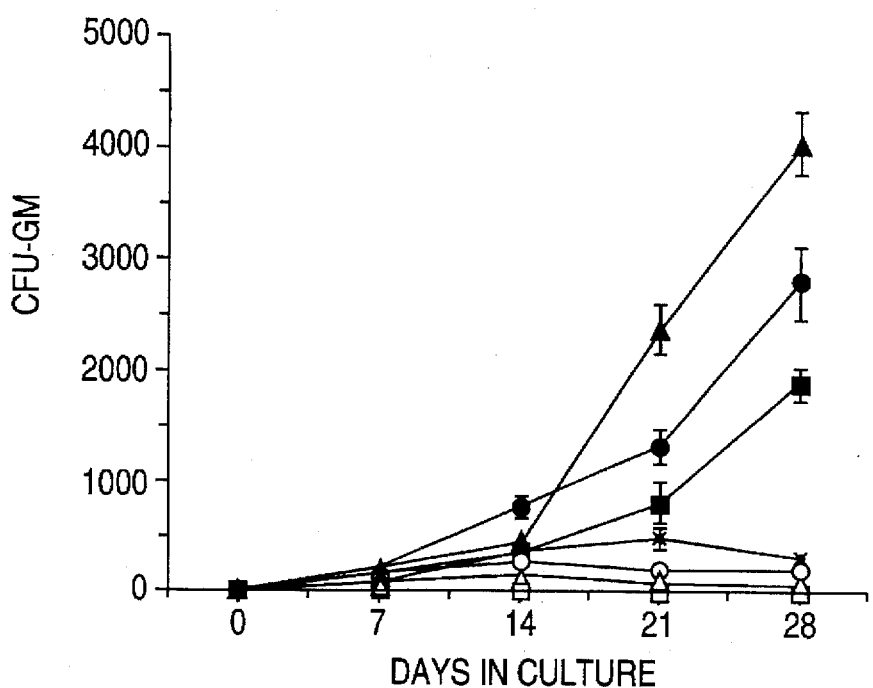
FIG. 5. Generation of CFU-GM and nucleated cells from sorted cell populations isolated on the basis of CD34 and HCC-1 expression. Closed triangles represent CD34$^{hi}$HCC-1$^+$ cells, closed circles represent CD34$^+$HCC-1$^{hi}$ cells, closed boxes represent CD34+HCC-1$^+$ cells, X represents CD34$^+$ cells, open triangles represent CD34$^{lo}$HCC-1$^+$ cells, open circles represent CD34$^+$HCC-1$^{lo}$ cells, and open boxes represent CD34$^+$HCC-1$^-$ cells. (A) Production of CFU-GM in the pre-CFU assay from sorted populations defined by the windows set in FIG. 4. (B) shows absolute numbers of nucleated cells generated by the various sorted populations. Data represent mean+SEM of three replicate cultures.

PATENT NO. : 5,677,136
DATED : October 14, 1997
INVENTOR(S) : Paul J. Simmons, Beth L. Hill, Benjamin P. Chen It is certified that error appears in the above-identified patent and that said Letters Patent is hereby corrected as shown below:

Figure 5A, Y Axis, "1000" should be --10,000--
Figure 5A, Y Axis, "2000" should be --20,000--
Figure 5A, Y Axis, "3000" should be --30,000--
Figure 5A, Y Axis, "4000" should be --40,000--
Figure 5A, Y Axis, "5000" should be --50,000--

Column 1, line 49, delete "." before --particular--

Column 2, line 5, delete "." before --substantially--
        line 7, insert "." after --cells --

Figure 1B:
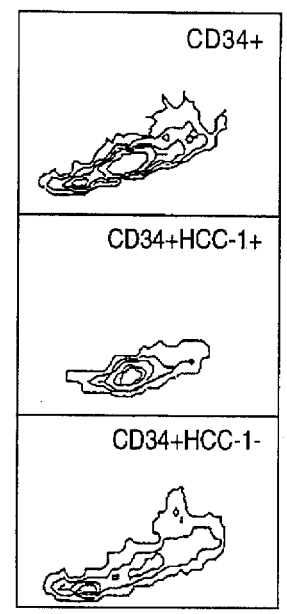
Figure 2A:
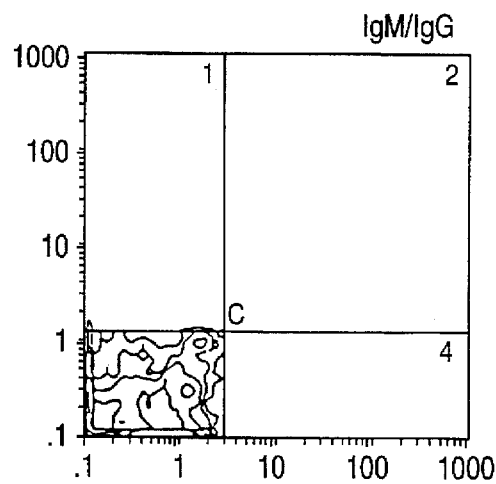
FIG. 2 is a three-color immunofluorescence analysis showing expression of HCC-1 by various subsets of CD34$^+$ cells. Contour plots were generated, each representing 10$^4$ CD34$^+$ events. Each plot shows the staining pattern of HCC-1 with a different lineage antigen, or rhodamine 123, with HCC-1 staining shown in the y-axis and the identified lineage marker on the x-axis. Panel A is IgM/IgG. Panel B is HCc-1/IgG. Panel C is YB5.B8. Panel D is CD3. Panel E is CD7. Panel F is CD33. Panel G is CD10. Panel H is CD19. Panel I is CD13. Panel J is CD38. Panel K is CD71. Panel L is Glycophorin-A. Panel M is CD45. Panel N is HLADL. Panel M is Rdodomine 123.
Figure 2B:
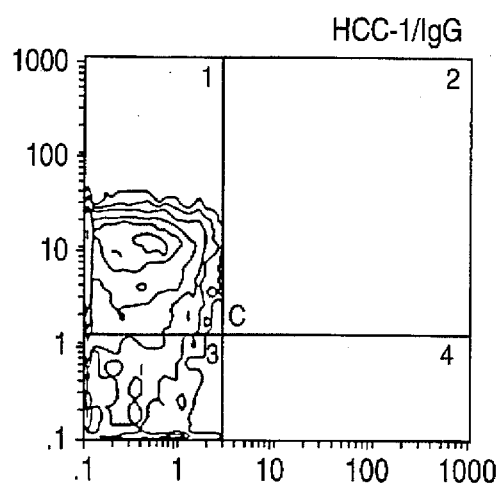
Figure 2C:
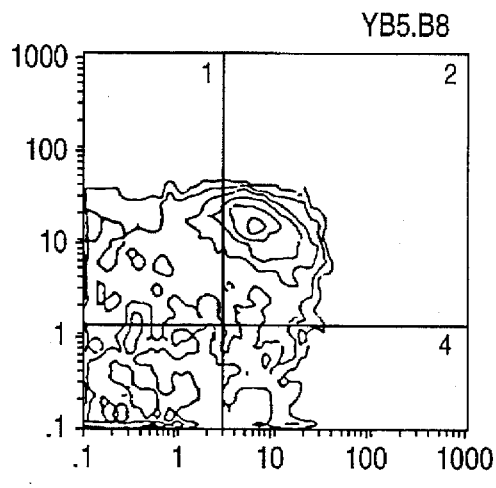
Figure 2D:
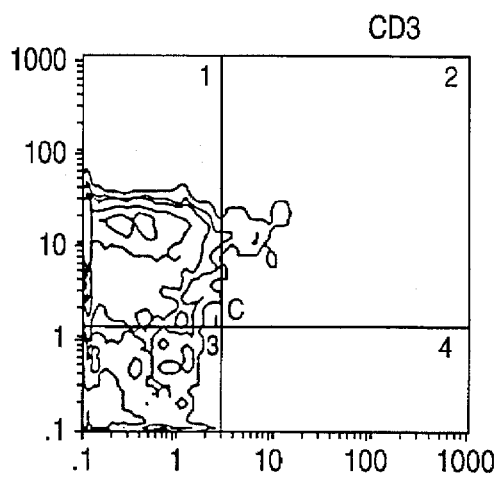
Figure 2E:
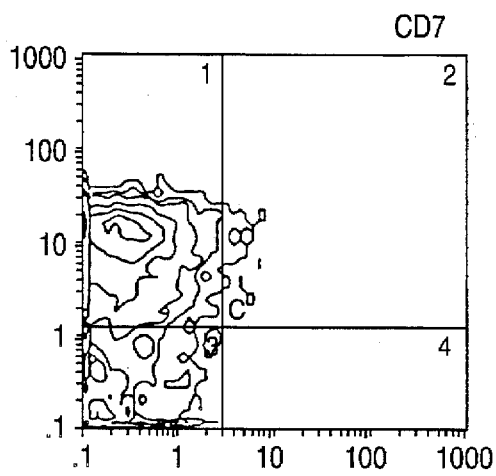
Figure 2F:
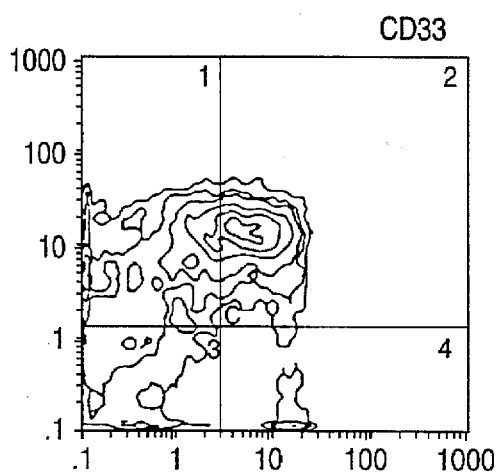
Figure 2G:
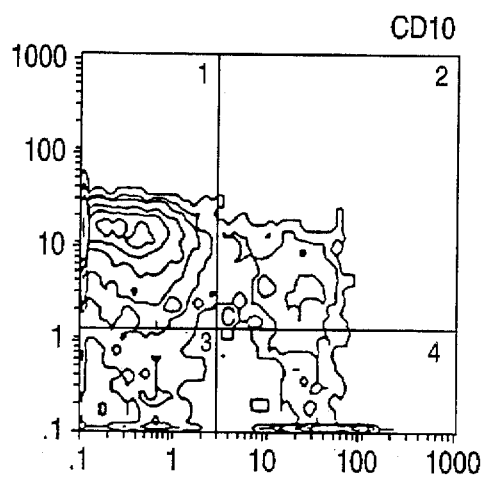
Figure 2H:
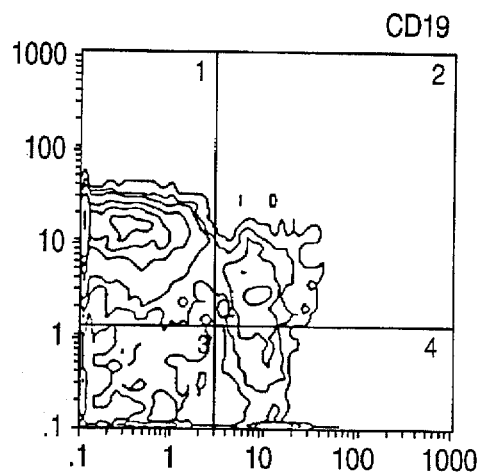
Figure 2I:
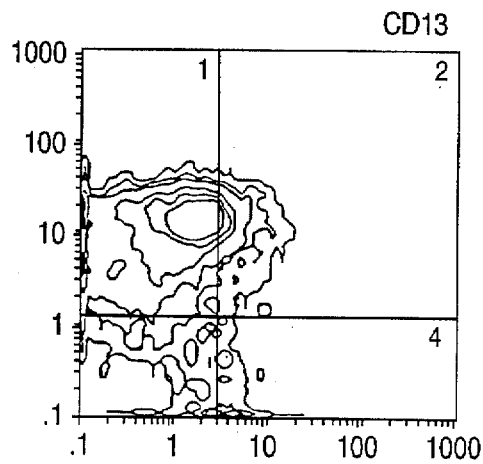
Figure 2J:
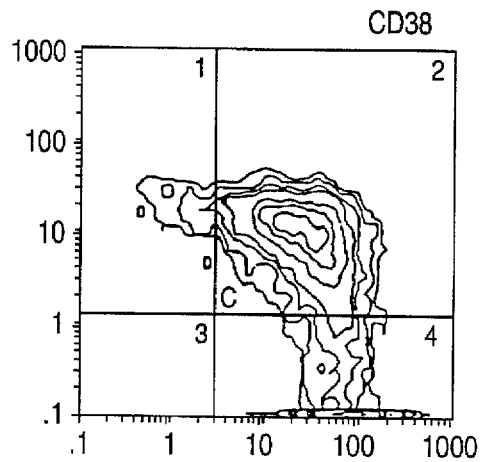
Figure 2K:
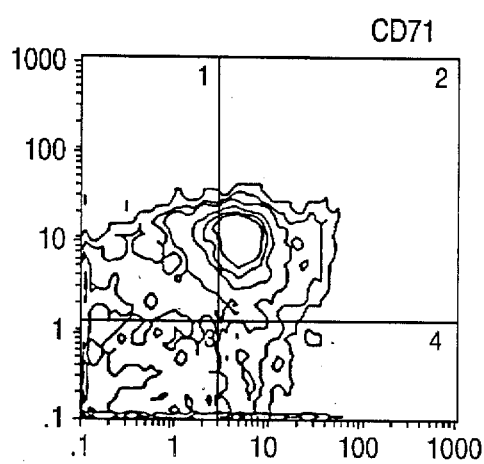
Figure 2L:
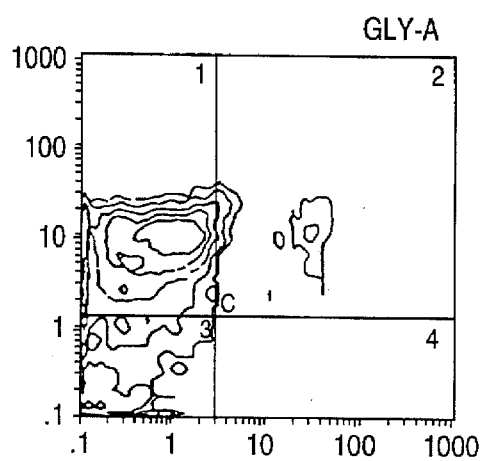
Figure 2M:
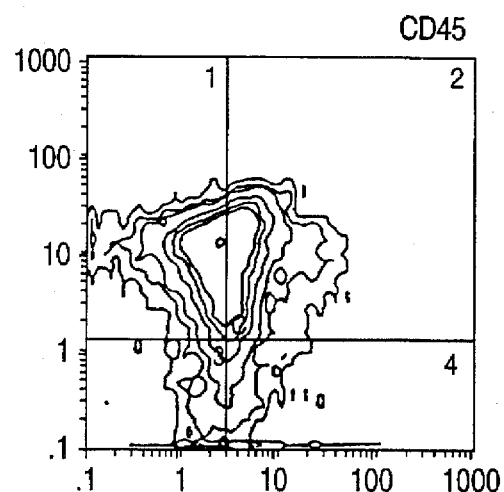
Figure 2N:
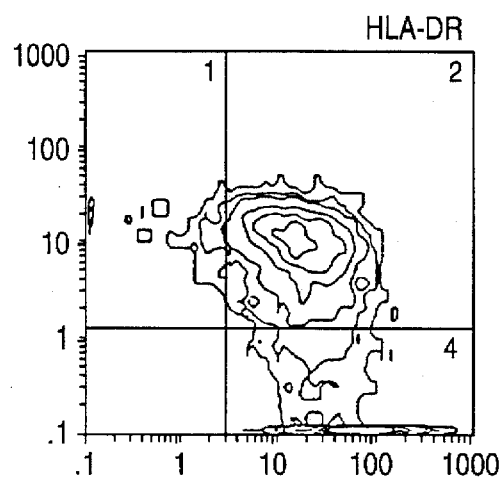
Figure 2O:
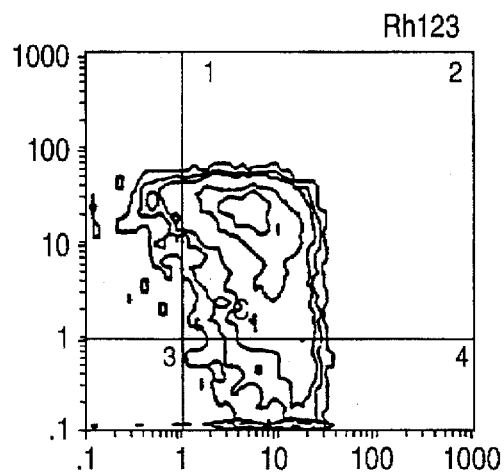
Figure 3A:
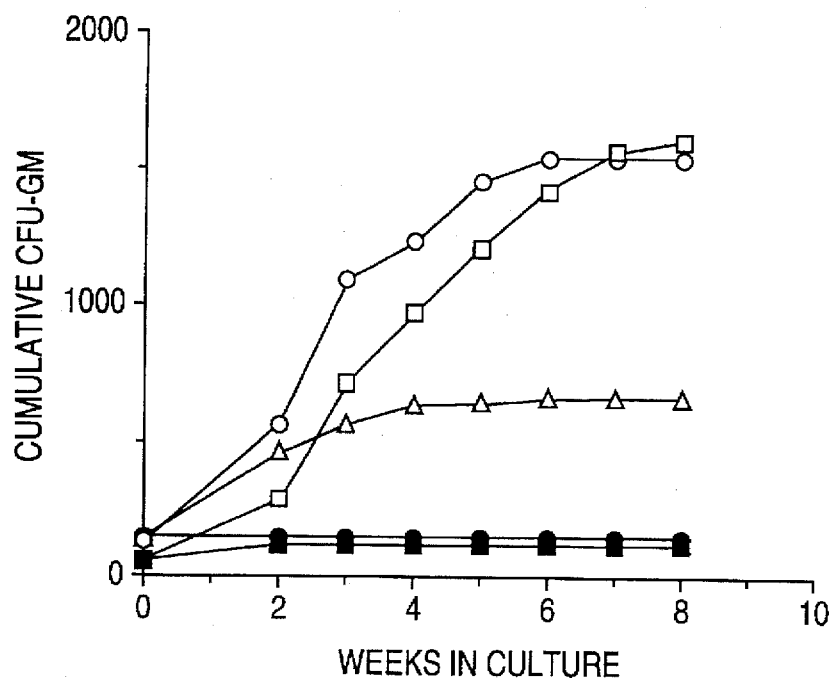
FIG. 3. Initiation of hematopoiesis in long-term bone marrow culture (LTBMC) by CD34$^+$rho$^{lo}$HCC-1$^+$ cells. open boxes represent CD34$^+$rho$^{lo}$HCC-1$^+$ cells, open circles represent CD34$^+$HCC-1$^+$ cells, open triangles represent CD34$^+$ cells, closed boxes represent CD34$^+$HCC-1$^-$ cells, and closed circles represent CD34$^+$HCC-1$^-$ cells. (A) shows cumulative production of CFU-GM by each population grown on stromal cell cultures, (B) shows the results of a pre-CFU assay in which populations of sorted cells were grown in the absence of stromal cells in a medium supplemented with cytokines.
Figure 3B:
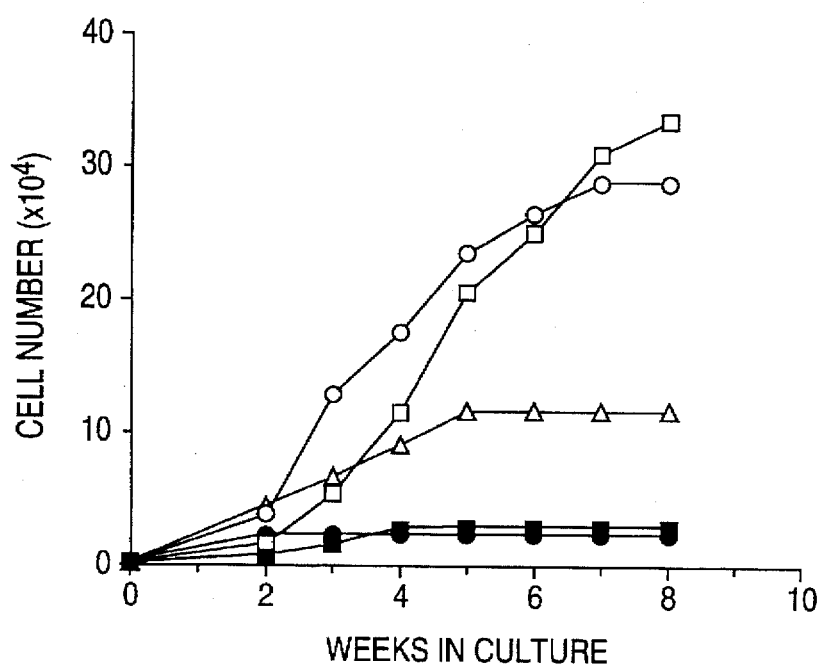
Figure 4A:
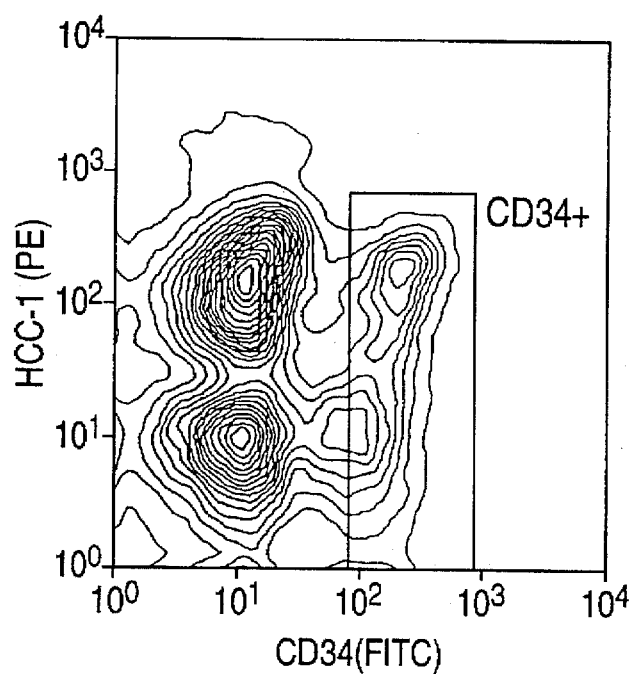
FIG. 4 shows two-color immunofluorescence analysis of CD34 and HCC-1 expression on bone marrow mononuclear cells (BMMNC). Cell sorting windows (boxes) are shown. In Panel A, the boxed region shows cells sorted as CD34$^+$. In Panel B, the boxed regions depict CD34$^+$HCC-1$^{hi}$ and CD34$^+$HCC-1$^{lo/-}$ cells. The boxed regions in Panel C show CD34$^{lo}$HCC-1$^+$ and CD34$^{hi}$HCC-1$^+$ cells. In Panel D, the boxed regions show CD34$^+$HCC-1$^{hi}$ and CD34$^+$HCC-1$^{lo}$ cells and CD34$^+$HCC-1$^-$.
Figure 4B:
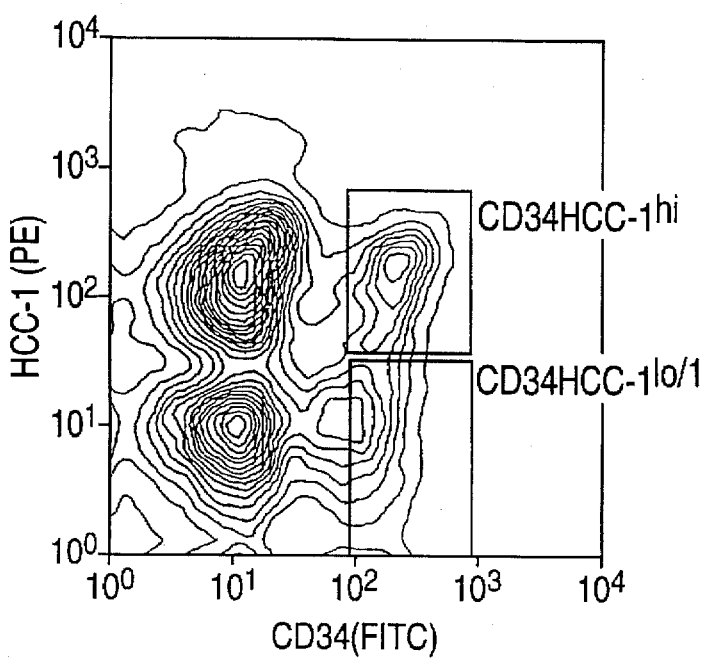
Figure 4C:
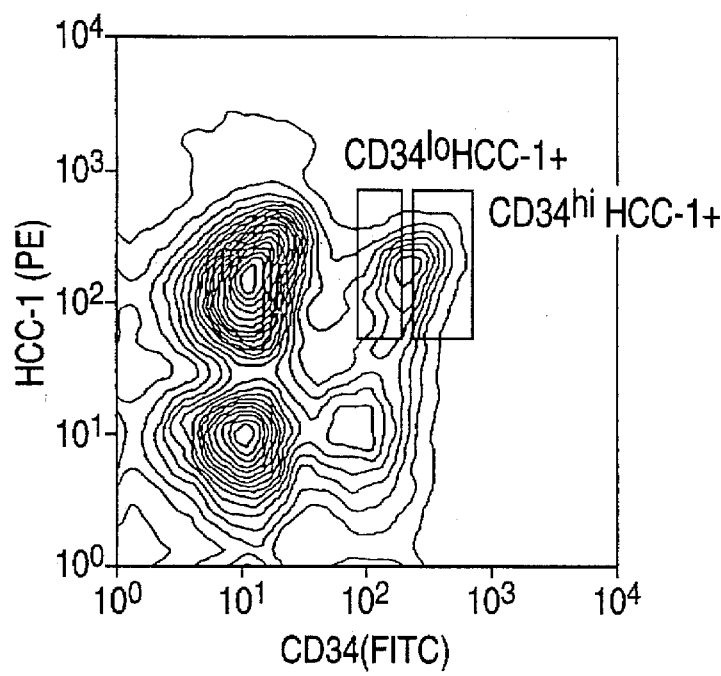
Figure 4D:
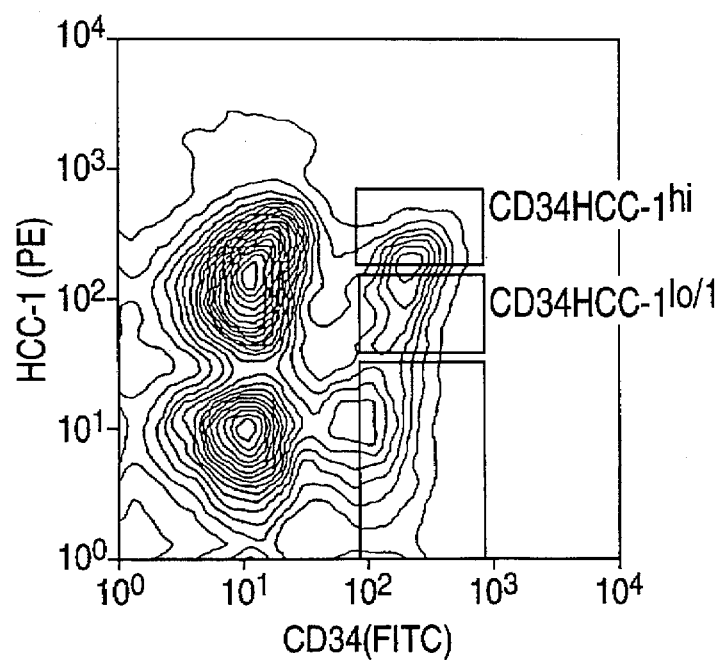

Column 3, line 8, "FIG. 1 depicts" should be --Figures 1A and 1B depict--
        line 10, "(A)" should be --Figure 1A--
        line 11, "(B)" should be --Figure 1B--
        line 14, "FIG. 2 is" should be --Figures 2A through 2O are--
        line 21, "HCc-1/IgG" should be --HCC-1/IgG--
        line 25, "Rdodomine" should be --Rhodomine--
        line 26, "FIG. 3." should be --Figures 3A and 3B.--
        line 28, "open" should be --Open--

UNITED STATES PATENT AND TRADEMARK OFFICE
CERTIFICATE OF CORRECTION

Figure 5B:
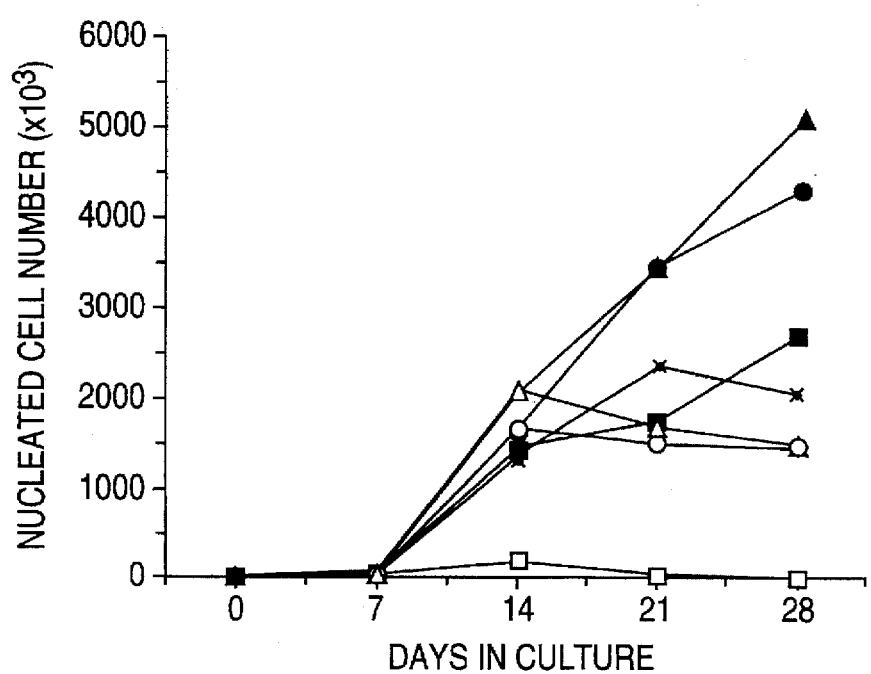
Figure 7A:
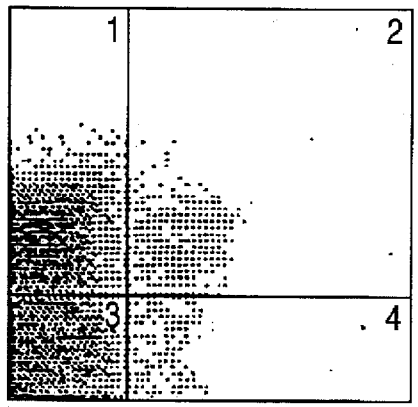
FIG. 7 depicts co-expression of CD34 and HCC-1 on leukemic bone marrow cells derived from different patients. Two-color fluorescence analyses are shown, using phycoerythrin-labelled HCC-1 and FITC-labelled CD34 antibodies.
Figure 7B:
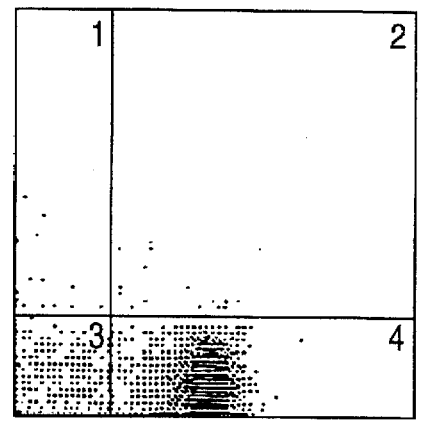
Figure 7C:
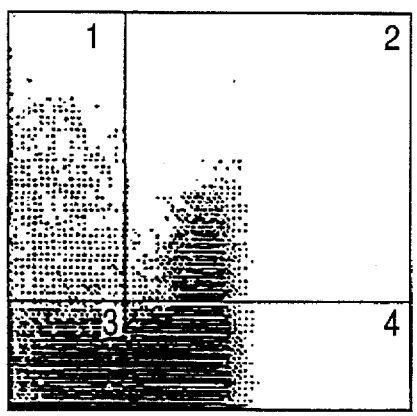
Figure 7D:
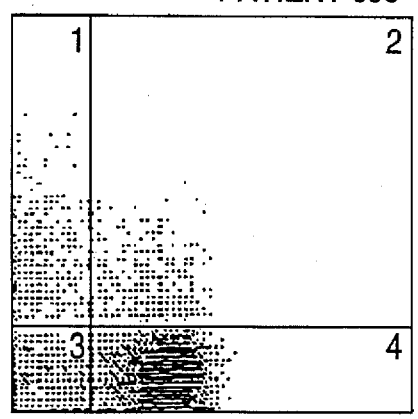
Figure 7E:
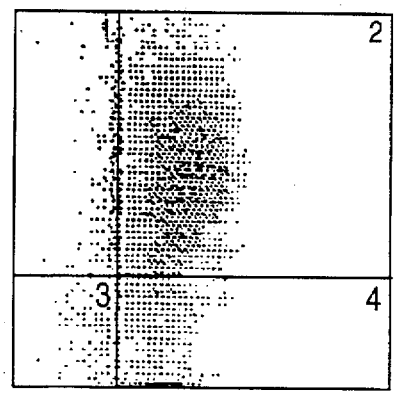
Figure 7F:
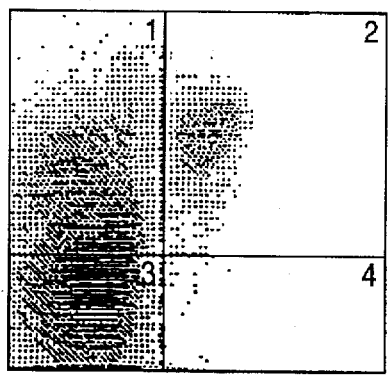
Figure 7G:
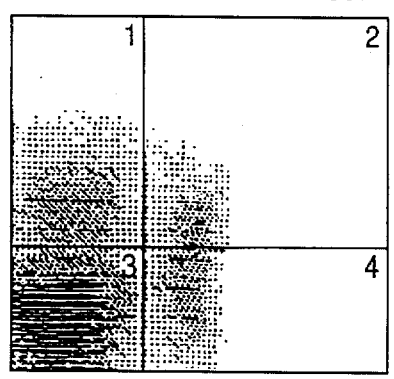
Figure 8C:
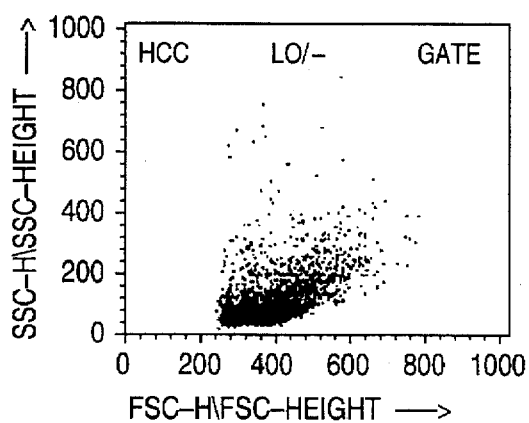
Figure 8D:
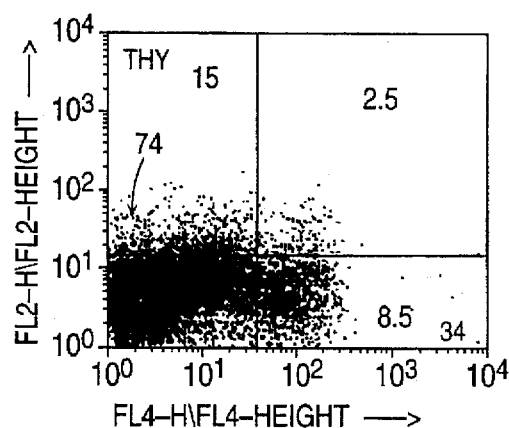
Figure 8E:
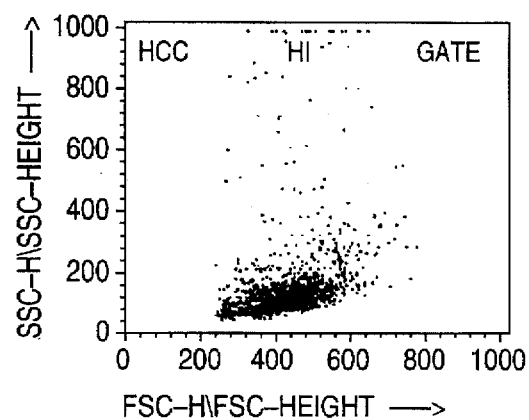
Figure 8F:
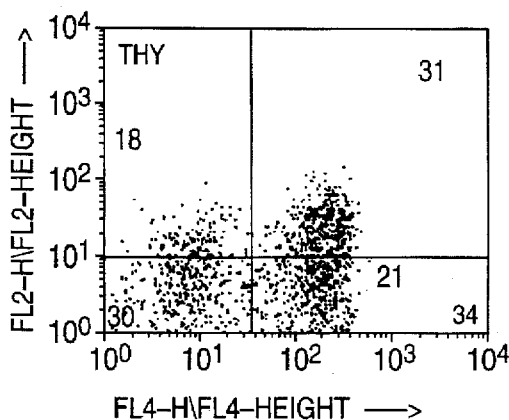
Figure 9A:
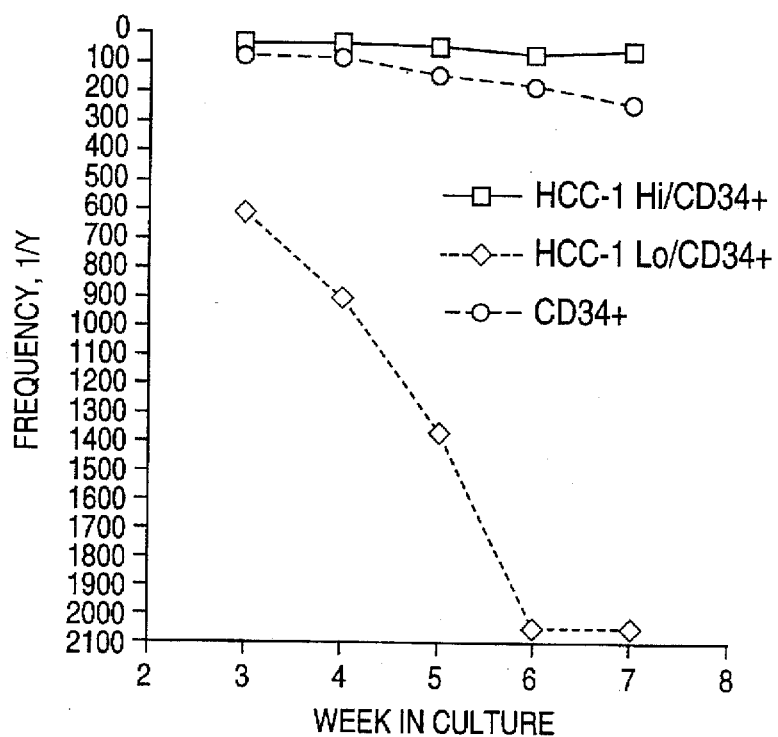
Figure 9B:
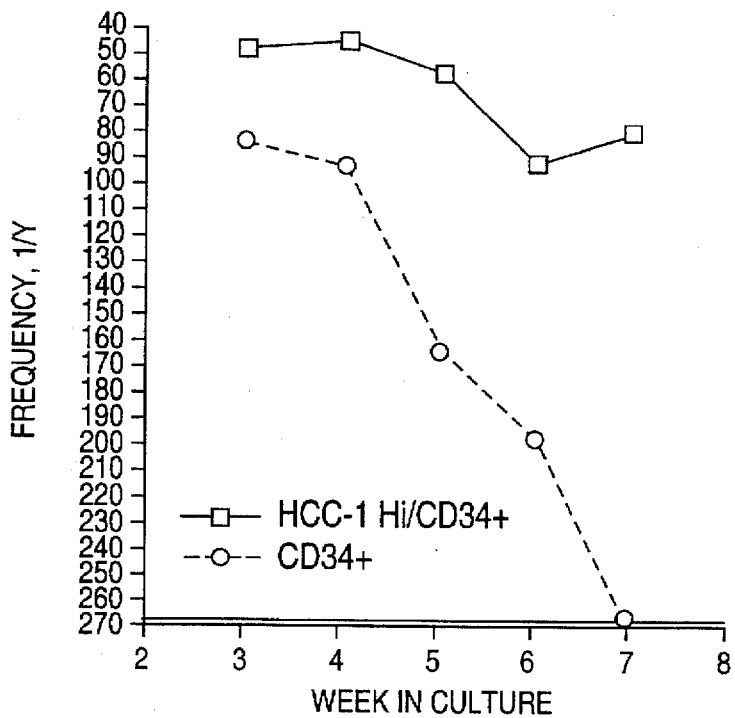

PATENT NO. : 5,677,136
DATED : October 14, 1997
INVENTOR(S) : Paul J. Simmons, Beth L. Hill, Benjamin P. Chen It is certified that error appears in the above-indentified patent and that said Letters Patent is hereby corrected as shown below:

line 31, "(A)" should be --Figure 3A--
    line 33, "(B)" should be --Figure 3B--
    line 37, "FIG. 4 shows" should be --Figures 4A through 4D show--
    line 46, "FIG. 5." should be --Figures 5A and 5B.--
    line 49, "dircles" should be --circles--
    line 50, "CD34+" should be --$CD34^+$--
    line 53, "(A)" should be --Figure 5A--
    line 55, "FIG. 4." should be --Figures 4A through 4D--
    line 55, "(B)" should be --Figure 5B--
    line 63, "FIG. 7 depicts" should be --Figures 7A through 7G depict--
Column 4, line 1, "Panel A" should be --Figure 7A--
    line 1, "Panel B" should be --Figure 7B--
    line 1, "Panel C" should be --Figure 7C--
    line 2, "Panel D" should be --Figure 7D--
    line 2, "Panel E" should be --Figure 7E--
    lines 2 and 3, "Panel F" should be --Figure 7F--
    line 3, "Panel G" should be --Figure 7G--
    line 4, "FIG. 8 depicts" should be --Figures 8A through 8F depict--
    line 6, "(A)" should be --Figure 8A--
    line 7, "(B)" should be --Figure 8B--
    line 8, "(C)" should be --Figure 8C--
    line 10, "(D)" should be --Figure 8D--
    line 11, "(E)" should be --Figure 8E--
    line 12, "(F)" should be --Figure 8F--
    line 14, "FIG. 9 depicts" should be --Figures 9A and 9B depict--
    line 15, "$CD34^{+HCC-1^{hi}}$" should be --$CD34^+HCC-1^{hi}$--
    line 16, "$CD34^{+HCC-1^{lol-}}$" should be --$CD34^+HCC-1^{lol-}$--

UNITED STATES PATENT AND TRADEMARK OFFICE
CERTIFICATE OF CORRECTION

PATENT NO. : 5,677,136

DATED : October 14, 1997

INVENTOR(S) : Paul J. Simmons, Beth L. Hill, Benjamin P. Chen

It is certified that error appears in the above-indentified patent and that said Letters Patent is hereby corrected as shown below:

lines 21 and 22, "HCc-1$^{hi}$/CD34$^+$" should be --HCC-1$^{hi}$/CD34$^+$--
line 24, "CD34$^{+HCC\text{-}1hi}$" should be --CD34$^+$HCC-1$^{hi}$--
line 25, "CD34$^{+HCC\text{-}1lol\text{-}}$" should be --CD34$^+$HCC-1$^{lol\text{-}}$--
line 28, "FIG. 11 depicts" should be --Figures 11A through 11H depict--
line 29, "CD34$^{+HCC\text{-}1hi}$" should be --CD34$^+$HCC-1$^{hi}$--
line 35, "CD34$^{+HCC\text{-}1hi}$" should be --CD34$^+$HCC-1$^{hi}$--
line 37, "FIG. 12 depicts" should be --Figures 12A through 12D depict--
line 38, "CD34$^{+Lin\text{-}}$" should be --CD34$^+$LIN$^-$--
line 47, "FIG. 13 depicts" should be --Figures 13A through 13D depict--
line 60, "american" should be --American--

Column 5, line 4, "capaciLies" should be capacities--
  lines 6 and 7, "subtraction" should be --subfraction--
  line 8, delete "." after --to--
  line 12, delete "." after --cell--
  line 13, delete "." after --subpopulation--
  line 27, delete "." after --bind--
  lines 62 and 63, "CD34$^{+Thy\text{-}1}$$^+$LIN$^-$" should be --CD34$^+$THY-1$^+$LIN$^-$--

Column 5-6, line 44, delete "P-gp"
  line 45, "P-gp" should appear directly above "Activity" on line 46

Column 6, line 15, "rho$^{l}$" should be --rho$^{lo}$--
  line 16, "CD34$^{+HCC\text{-}1+}$" should be --CD34$^+$HCC-1$^+$--
  line 31, "Stands" should be --stands--
  line 32, "b6th" should be --both--

UNITED STATES PATENT AND TRADEMARK OFFICE
CERTIFICATE OF CORRECTION

PATENT NO. : 5,677,136

DATED : October 14, 1997

INVENTOR(S) : Paul J. Simmons, Beth L. Hill, Benjamin P. Chen

It is certified that error appears in the above-indentified patent and that said Letters Patent is hereby corrected as shown below:

Column 7, line 10, "Composition" should be --composition--
 line 36, "c6mpete" should be --compete--
 line 47, "hematopdietic" should be --hematopoietic--

Column 8, line 34, "allophycbcyanins" should be --allophycocyanins--
 line 54, "HCC-1antibodies" should be --HCC-1 antibodies--
 line 61, "cellb" should be --cells--
 line 61, "CD34$^{+HCC-1hi}$" should be --CD34$^+$HCC-1$^{hi}$--
 line 65, delete "." after --and--

Column 10, line 35, "CD34$^{+HCC-1hi}$" should be --CD34$^+$HCC-1$^{hi}$--
 line 54, "scia/scid" should be --scid/scid--
 line 61, "CD34$^{+HCC-1lol-}$" should be --CD34$^+$HCC-1$^{lol-}$--
 line 64, "CD34$^{+HCC-1hi}$" should be --CD34$^+$HCC-1$^{hi}$--

Column 11, line 11, "CD34$^{+HCC-1hi}$" should be --CD34$^+$HCC-1$^{hi}$--
 line 14, "CD34$^{+HCC-1hi}$" should be --CD34$^+$HCC-1$^{hi}$--
 line 22, "CD34$^{+HCC-1hi}$" should be --CD34$^+$HCC-1$^{hi}$--
 line 37, "CD34$^{+HCC-1hi}$" should be --CD34$^+$HCC-1$^{hi}$--
 line 39, "hematopoieti, c" should be --hematopoietic--
 lines 39 and 40, "CD34$^{+HCC-1hi}$" should be --CD34$^+$HCC-1$^{hi}$--
 line 44, "CD34$^{+HCC-1hi}$" should be --CD34$^+$HCC-1$^{hi}$--
 line 52, "CD34$^{+HCC-1hi}$" should be --CD34$^+$HCC-1$^{hi}$--

UNITED STATES PATENT AND TRADEMARK OFFICE
CERTIFICATE OF CORRECTION

PATENT NO. : 5,677,136

DATED : October 14, 1997

INVENTOR(S) : Paul J. Simmons, Beth L. Hill, Benjamin P. Chen

It is certified that error appears in the above-indentified patent and that said Letters Patent is hereby corrected as shown below:

Column 12, line 19, "g/dn)." should be --g/dL).--
        line 22, "(PB)-at" should be --(PB) at--
        line 23, "platelet-rieh" should be --platelet rich--

Column 13, line 15, "(TS, Coulter)," should be --(T8, Coulter),--
        line 21, delete "Class" (first occurrence)
        line 24, "WEMGll" should be --WEMG11--
        line 31, "Miles)/" should be --Miles).--
        line 52, "μheavy" should be μ heavy"

Column 14, line 8, delete "." after --Bone--

Column 15, line 29, "(Q-CSF)" should be --(G-CSF)--
        line 36, "each,well" should be --each well--
        line 42, "celis" should be --cells--
        line 58, "($CA^{2+}$," should be --($CA^{2+}$-,"

Column 16, line 22, "69.1 5.9%" should be --69.1±5.9%--
        line 25, "42 65%" should be --42-65%--
        line 26, "$CD34^{+HCC-}1^{+}$" should be --$CD34^{+}HCC-1^{+}$--
        line 26, "$CD34^{+HCC-}1^{-}$" should be --$CD34^{+}HCC-1^{-}$--
        line 28, "Light" should be --light--
        lines 29-30, "$CD34^{+HCC-}1^{-}$" should be --$CD34^{+}HCC-1^{-}$--
        line 48, "ckit" should be --c-kit--
        line 52, "$CD19^{+}$" should be --$CD19^{+}$--

UNITED STATES PATENT AND TRADEMARK OFFICE
CERTIFICATE OF CORRECTION

PATENT NO. : 5,677,136
DATED : October 14, 1997
INVENTOR(S) : Paul J. Simmons, Beth L. Hill, Benjamin P. Chen It is certified that error appears in the above-indentified patent and that said Letters Patent is hereby corrected as shown below:

Column 17, Table 3-continued, line 2,
"(2.5-7.0) (2.7-9.8) (88-100" should be
--(2.5-7.0) (2.7-9.8) (88-100)-- line 13,
"CD38 91.6 ± 3.2 86.9 41 2.6 60.6 ± 4.6" should be
--CD38 91.6 ± 3.2 86.9 ± 2.6 60.6 ± 4.6-- line 32, "FIGS. 12 and 13" should be --Figures 12A through 12D and 13A through 13D-- line 66, "CD34$^{+HCC\text{-}1+}$" should be --CD34$^+$HCC-1$^+$--
line 66, "CD34$^{+HCC\text{-}1-}$" should be --CD34$^+$HCC-1$^-$--

Column 18, Table 5, line 7,
"CD34$^+$HCC-1$^+$ 70/3 ± 5.1 102 ± 15.7 0" should be
--CD34$^+$HCC-1$^+$ 70.3 ± 5.1 102 ± 15.7 0 line 32, "CD34$^{+HCC\text{-}1+}$" should be --CD34$^+$HCC-1$^+$--
line 33, "multicentric.type" should be --multicentric type--
line 38, "(CFUGEMM)" should be --(CFU-GEMM)--
line 41, "CD34$^{+HCC\text{-}1+}$" should be --CD34$^+$HCC-1$^+$--
line 41, "CD34$^{+HCC\text{-}1-}$" should be --CD34$^+$HCC-1$^-$--
line 45, "L6ng-term" should be --Long-term--

UNITED STATES PATENT AND TRADEMARK OFFICE
CERTIFICATE OF CORRECTION

PATENT NO. : 5,677,136
DATED : October 14, 1997
INVENTOR(S) : Paul J. Simmons, Beth L. Hill, Benjamin P. Chen It is certified that error appears in the above-indentified patent and that said Letters Patent is hereby corrected as shown below:

line 53, "Tershappen" should be --Terstappen--
line 55, "CD34$^{+Rho^{lo}}$" should be --CD34$^+$Rho$^{lo}$--
line 56, "FIG. 2" should be --Figures 2F, 2J, 2N or 2O, respectively,--
lines 58-59, "CD34$^{+HCC\text{-}1^+}$" should be --CD34$^+$HCC-1$^+$--
line 59, "CD34$^{+HCC\text{-}1^-}$" should be --CD34$^+$HCC-1$^-$--
line 64, "CD34$^{+HCC\text{-}1^+}$" should be --CD34$^+$HCC-1$^+$--

Column 19, line 2, "CD34$^{+Rho^{lo}}$" should be --CD34$^+$Rho$^{lo}$--
line 3, "FIG.2 illustrates" should be -Figures 2A through 2O illustrate--
line 4, "The" should be deleted
line 4, "Rho$^{lo}$HCC-1$^-$" should be --Rho$^{lo}$HCC-1$^+$--
line 6, "FIG. 3" should be --Figures 3A and 3B--
lines 7-8, "CD34$^+$$_{Rho}$$^{lo}$" should be --CD34$^+$Rho$^{lo}$--
lines 8-9, "CD34$^+$$_{Rho}$$^{lo}$" should be --CD34$^+$Rho$^{lo}$--
line 11, "CD34$^{+HCC\text{-}1^+}$" should be --CD34$^+$HCC-1$^+$--
line 11, "CD34$^{+HCC\text{-}1^-}$" should be --CD34$^+$HCC-1$^-$--
line 15, "FIG. 5 shows" should be --Figures 5A and 5B show--
line 16, "CD34$^{+HCC\text{-}1^+}$" should be --CD34$^+$HCC-1$^+$--
lines 16-17, "sustaihed" should be --sustained--
line 18, "CD34$^{+HCC\text{-}1^+}$" should be --CD34$^+$HCC-1$^+$--

UNITED STATES PATENT AND TRADEMARK OFFICE
CERTIFICATE OF CORRECTION

PATENT NO. : 5,677,136
DATED : October 14, 1997
INVENTOR(S) : Paul J. Simmons, Beth L. Hill, Benjamin P. Chen It is certified that error appears in the above-indentified patent and that said Letters Patent is hereby corrected as shown below:

line 19, "CD34$^{+HCC-1hi}$" should be --CD34$^+$HCC-1$^{hi}$--
line 19, "CD34$^{+HCC-1lo}$" should be --CD34$^+$HCC-1$^{lo}$--
line 20, "FIG. 4." should be --Figures 4A through 4D.--
line 21, "FIG. 5." should be --Figures 5A and 5B.--
line 23, "CD34$^{+HCC-1hi}$" should be --CD34$^+$HCC-1$^{hi}$--
line 30, "ahtibodywas" should be --antibody was--
line 31, "(BMMNd)" should be --(BMMNC)--
line 32, "(pBMNC)" should be --(PBMNC)--
line 35, delete "." after --blood--
line 63, "Leohie" should be --Leonie--
line 63, "Center" should be --Centre--

Column 20, line 11, "exampl&s" should be --examples--
line 11, "FIG. 7" should be --Figures 7A through 7G--
line 66, "1231   6/.2   1   0.3   0.1" should be --1231   6.2   1   0.3   0.1--

Column 21, line 56, "Rayher" should be --Rayner--
line 67, "pdpulations" should be --populations--

Column 22, line 5, "Genbahk" should be --Genbank--
line 16, "Warrow" should be --Marrow--
line 16, delete "." after --cells--

UNITED STATES PATENT AND TRADEMARK OFFICE
CERTIFICATE OF CORRECTION

PATENT NO. : 5,677,136

DATED : October 14, 1997

INVENTOR(S) : Paul J. Simmons, Beth L. Hill, Benjamin P. Chen

It is certified that error appears in the above-indentified patent and that said Letters Patent is hereby corrected as shown below:

Column 23, line 3, insert ">" before --50--
        line 11, "FIG. 9" should be --Figures 9A and 9B--
        line 65, "2487" should be --2497--

Column 24, line 27, "FIG. 11," should be --Figures 11A through 11H,--
        line 29, insert "$\geq 1\%$" before --donor-derived--
        line 30, "$CD34^{+HCC-1hi}$" should be --$CD34^+HCC-1^{hi}$--
        line 45, "byway" should be --by-way--
        line 53, "insert "a" before --subpopulation--
        line 53, "hematopoiefic" should be --hematopoietic--
        line 55, delete "," after --obtaining-- line 62, insert "from the population of human hematopoietic cells" after --separating--
        line 66, "accoraing" should be --according--

Column 25, line 5, "$rho^h$" should be --$rho^{lo}$--
        line 23, "Subpopulation" should be --subpopulation--
        line 30, "5" should be --10--

Column 26, line 31, "epitiope" should be --epitope--

Signed and Sealed this

Twenty-eighth Day of July, 1998

Attest:

BRUCE LEHMAN

Attesting Officer      Commissioner of Patents and Trademarks